(12) United States Patent
Chan et al.

(10) Patent No.: US 6,676,988 B2
(45) Date of Patent: *Jan. 13, 2004

(54) RADIOACTIVELY COATED DEVICES

(75) Inventors: Albert Chan, Ottawa (CA); Stephen M. Oelsner, Ontario (CA); Thomas J. Simpson, Ontario (CA); Sonia Corrent, Ottawa (CA)

(73) Assignee: MDS (Canada) Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/014,606

(22) Filed: Dec. 14, 2001

(65) Prior Publication Data

US 2002/0169353 A1 Nov. 14, 2002

Related U.S. Application Data

(63) Continuation-in-part of application No. 09/559,538, filed on Apr. 28, 2000, now Pat. No. 6,394,945, which is a continuation-in-part of application No. 08/995,524, filed on Dec. 22, 1997, now Pat. No. 6,103,295.

(51) Int. Cl.$^7$ .......................... A61L 27/00; A61L 27/54; B05D 5/00
(52) U.S. Cl. ...................... 427/2.24; 427/2.1; 427/2.14; 427/2.25; 427/2.28; 427/2.3; 427/212; 427/372.2; 427/383.1; 427/383.7; 427/404; 427/405; 427/435; 427/436
(58) Field of Search ................ 427/2.1, 25.14, 427/2.24, 2.25, 2.28, 2.3, 212, 372.2, 383.1, 383.7, 404, 405, 435, 436

(56) References Cited

U.S. PATENT DOCUMENTS

| | | |
|---|---|---|
| 2,711,484 A | 6/1955 | Knapp et al. |
| 2,915,406 A | 12/1959 | Rhoda et al. |
| 3,582,656 A | 6/1971 | Koehler |
| 3,769,511 A | 10/1973 | Delacy |
| 3,974,322 A | 8/1976 | Drabkina et al. |

(List continued on next page.)

FOREIGN PATENT DOCUMENTS

| | | |
|---|---|---|
| JP | 48017384 | 5/1973 |
| WO | WO 93/04735 | 3/1993 |

OTHER PUBLICATIONS

Madigan et al., Sonochemical Stripping Voltammetry, Anal. Chem. 1995, 67: 2781–2786.

(List continued on next page.)

Primary Examiner—Shrive P. Beck
Assistant Examiner—Jennifer Kolb Michener
(74) Attorney, Agent, or Firm—Sughrue Mion, PLLC

(57) ABSTRACT

This invention relates to radioactively coated devices, preferably radioctively coated medical devices. These coated devices are characterized as having a low rate of leaching of the radioisotope from the surface of the coated device and a uniform radioactive coating, and are therefore suitable for use within biological systems. Methods for coating a device with a radioisotope comprising are also disclosed. One method comprises immersing the device within a solution containing a $\gamma$, $\beta^+$, $\alpha$, $\beta^-$ or $\epsilon$ (electron capture) emitting radioisotope, then exposing the immersed substrate to tuned vibrational cavitation to produce a coated substrate. A second method involves coating a substrate using electroless plating, and yet a third method involves the use of electroplating a radioisotope onto a substate of interest. With these methods, the coating procedures are followed by baking the coated substrate at a temperature below the recrystallization temperature of the substrate. Substrates coated using the methods of this invention exhibit very low rates of leaching of the coated radioisotope, and are suitable for use within medical applications, for example as stents, catheters, seeds, protheses, vavles, staples and other wound closure devices, where a localized therapeutic treatment is desired.

30 Claims, 11 Drawing Sheets

U.S. PATENT DOCUMENTS

| | | | |
|---|---|---|---|
| 4,169,186 A | 9/1979 | Tazaki et al. | |
| 4,702,228 A | 10/1987 | Russell, Jr. et al. | |
| 4,815,449 A | 3/1989 | Horowitz | |
| 4,818,307 A | 4/1989 | Mori et al. | |
| 4,900,368 A | 2/1990 | Brotz | |
| 4,994,013 A * | 2/1991 | Suthanthiran et al. | 600/8 |
| 5,059,166 A | 10/1991 | Fischell | |
| 5,163,896 A | 11/1992 | Suthanthiran et al. | |
| 5,176,617 A | 1/1993 | Fischell et al. | |
| 5,197,940 A | 3/1993 | Sievert et al. | |
| 5,213,561 A | 5/1993 | Weinstein et al. | |
| 5,342,283 A | 8/1994 | Good | |
| 5,405,309 A | 4/1995 | Carden, Jr. | |
| 5,479,969 A | 1/1996 | Hardie et al. | |
| 5,484,384 A | 1/1996 | Fearnot | |
| 5,498,227 A | 3/1996 | Mawad | |
| 5,575,749 A | 11/1996 | Liprie | |
| 5,618,266 A | 4/1997 | Liprie | |
| 5,707,332 A | 1/1998 | Weinberger | |
| 5,851,315 A * | 12/1998 | Strathearn et al. | 148/239 |
| 5,977,163 A * | 11/1999 | Li et al. | 514/449 |
| 6,010,445 A | 1/2000 | Armini et al. | |
| 6,013,099 A | 1/2000 | Dinh et al. | |
| 6,042,600 A | 3/2000 | Rosenthal et al. | |
| 6,045,495 A | 4/2000 | Weinberger | |
| 6,103,295 A * | 8/2000 | Chan et al. | 427/5 |
| 6,149,574 A * | 11/2000 | Trauthen et al. | 600/3 |
| 6,187,037 B1 | 2/2001 | Satz | |
| 6,287,249 B1 * | 9/2001 | Tam et al. | 600/3 |
| 6,394,945 B1 * | 5/2002 | Chan et al. | 600/3 |

OTHER PUBLICATIONS

Wizemann et al., Cancellation of Matrix Effects and Calibration by Isotope Dilution in Isotope–Selective Diode Laser Atomic Absorption Spectrometry, Anal. Chem. 1997, 69: 4291–4293.

Arlinghaus et al., Multiplexed DNA Sequencing and Diagnostics by Hybridization with Enriched Stable Isotope Labels, Anal. Chem. 1977, 69:1510–1517.

Fehsenfeld et al., Radionuclide Technique in Mechanical Engineering in Germany, Journal of Radioanalytical and Nuclear Chemistry: Articles, vol. 160, No. 1: 141–151 (1992).

Eichholz et al., Adsorption of Ions in Dilute Aqueous Solutions on Glass and Platic Surfaces, vol. 37, No. 7: 863–868, Jun. 1965.

Wong et al., Intracoronary stents, Current Opinion in Cardiology, 10:404–411, 1995.

Carter et al., Effects of Endovascular Radiation from a B–Particle–Emitting Stent in a Porcine Coronary Restonosis Model, Circulation 94:2364–68 (1996).

Fischell et al., The Beta–Particle–Emitting Radioisotope Stents (Isotent): Animal Studies and Planned Clinical Trials, The American Jouranl of Cardiology, vol. 78 (3A): 45–50, 1996.

Hehrlein et al., Low–Dose Radioactive Endovascular Stents Prevent Smooth Muscle Cell Proliferation and Neointimal Hyperplasia in Rabbits, Circulation 92: 1570–75, 1995.

Violaris et al., Endovascular stents: a "break through technology", future challenges, International Jornal of Cardiac Imagining 13:3–13, 1997.

Prestwich, Analytic presentation of the dose from a $^{32}$P–coated stent, Med. Phys. 23(1): 9–13, Jan., 1996.

Janicki et al., Radiation dose from a phosphorous–32 impregnated wire mesh vacular stent, Med. Phys. 24(3): 437–445, 1997.

Blair, Alan, AT&T & Bell Laboratories; ASM International Handbook, The Materials Information Society, "Surface Engineering"–vol. 5, Feb. 1996; pp. 245–246, 251–254.

Lide, David R., Ph.D., "CRC Handbook of Chemistry and Physics", 71$^{st}$ edition, 1990–1991.

Cheever, Dale G., General Motor Research Laboratories, Formation and Growth of Zinc Phosphate Coatings, vol. 39–No. 504: 1–13, Jan. 1967.

Uemiya et al., Preparation of Thin Palladium Films by Use of an Electroless Plating Technique, The Chemical Society of Japan, vol. 6, 1990, pp. 669–675 and abstract.

Uemiya et al., Preparation of Palladium Composite Membrane using CVD Technique, Hyomen Gijutsu 1994, (1995 CAPLUS Abstract).

Nawafune et al., Electroless Palladium Plating from Ethylenediamine Complex Bath using Formic Acid as a Reducing Agent, Ishihara Chemical Co., Ltd., Japan 1998, pp. 1–5 (abstract).

Keuler et al., Optimizing Palladium Conversion in Electroless Palladium Plating of Alumina Membranes, Plat. Surf. Finish., 84: 34–40, 1997.

* cited by examiner

RADIOACTIVELY COATED DEVICES

The is a Continuation-In-Part of application Ser. No. 09/559,538, filed Apr. 28, 2000 now U.S. Pat. No. 6,394,945 which is a Continuation-In-Part of application Ser. No. 08/995,524 filed Dec. 22, 1997 now U.S. Pat. No. 6,103,295.

The present invention relates to a method of producing a uniform distribution of radioisotope on a surface of a device. Furthermore, this invention is directed to coated products prepared using the disclosed method. More specifically, this invention is directed at permanently affixing a radioisotope of interest on the surface of a medical device.

BACKGROUND OF THE INVENTION

In recent years the treatment of medical ailments using implantable devices treated with radioactivity has gained prominence throughout the medical community. This is because the antiproliferative effect of ionizing radiation has been recognized, and used, to reduce proliferative cell growth including, cancer cell growth. An advantage of using radioactive devices to apply the radiotherapy treatment is that the dose of radioactivity is localized and minimizes the total overall dose given to the patient. For example, it has been proposed that over 95% of the radiation dose is delivered with 5–6 mm of the implantation site (Fishell et al 1996, which is incorporated by reference). Typical applications of medical devices, treated so that they are radioactive, include the treatment of localized lesions using radioactive implants, stents and/or brachytherapy wires, or for example, the treatment of aberrant cell growth using radioactively treated catheters, or catheters capable of accepting radioactive inserts (U.S. Pat. Nos. 5,213,561; 5,484,384; 5,498,227; 5,575,749; WO 93/04735; Violaris et al 1997; Carter et al 1996; Fischell et al 1996; Hehrlein et al 1995, Wong and Leon 1995, which are all incorporated by reference). Other medical devices that are useful in treatment of cancers and the like include implantable radioactive sources, such as seeds etc (U.S. Pat. Nos. 4,815,449; 4,994,013; 5,342,283; 5,405,309, which are incorporated by reference).

Several important criteria for a radioactively treated medical device have been identified. It is generally desired within the art that medical devices treated with radioactivity exhibit a uniform, homogeneous distribution of radioisotope over the length and breadth of the device, and that the radioisotope be permanently affixed to the device and not leach out and contaminate the surrounding tissues when the device is implanted. The production of radioactive seeds comprising encapsulated radioactive sources (see U.S. Pat. Nos. 4,815, 449; 4,994,013; 5,163,896; 5,575,749; WO 93/04735, which are incorporated by reference) meets the criteria for reducing the potential of isotope leaching during in vivo use, however, these devices result in high levels of microlocalized emissions of radiation at the location of the radioactive seed within the implant. Therefore, a significant drawback with such a device is the non-homogeneous delivery of ionizing radiation. In order to produce devices that exhibit negligible leaching and uniform isotope distribution, methods of ion implantation, wherein the isotope is imbedded within the structure of the stainless steel or metal device have been explored (U.S. Pat. No. 5,059,166; Fischell et al 1996; Violaris et al 1997). In addition, yields are low and difficult to control. Heavier elements are more difficult to ionize, requiring highly specialized, low reliability ion sources. As well, radioactive contamination of the ion source makes maintenance a safety hazard. Typical methods for the preparation of radioactively treated medical devices include bombarding non-radioactive metallic substrate with radioactive ions or transmutating the base material with protons or neutrons creating radioisotopes internally (e.g. U.S. Pat. Nos. 4,702,228; 5,405,309). Published work on pilot scale manufacturing methods of stents produced in this manner have been disclosed (Fehsenfeld et al 1991), however, these approaches for the preparation of radioactive devices are limited since they are one-at-a-time processes or involve extensive specialized equipment. Furthermore, only a range of substrates can be used that are compatible with the implantation technologies thereby limiting the selection of materials that can be used for the preparation of radioisotope-treated devices. For example palladium, enriched with palladium-102 can be used for transmutation by exposure to neutron flux, to produce palladium-103 (e.g. U.S. Pat. No. 4,702,228). Transmutation technologies utilizing protons or neutrons would also result in significant undesirable isotopes and associated radiation exposure to the patient in vivo. Furthermore, recovery costs for transmutation methods are high.

A dominant barrier for the application of the use of radioactively treated medical devices has been the lack of a commercially viable method for affixing the radioisotope to a medical device that meets the low leaching criteria required within the art.

Several reports comment, or mention in passing, the option of coating the surface of a medical device such as a stent with a radioisotope of interest (e.g. U.S. Pat. No. 5,213,561; Hehrlein 1995). However, no methods are provided for the preparation of such coated devices, nor are there any methods provided that could be used for the preparation of coated devices that would be suitable for medical application. Rather due to the stringent requirements of negligible, or no, isotope leaching from the radioactive device (e.g. Fischell et al 1996), coated medical devices have received poor reception within the art as it is expected that the coated radioisotope will leach while implanted in vivo. The generally accepted levels of isotope leaching for a coated medical device must be less than about 5% of the total isotope applied to the substrate. Preferably the amount of leachable radioisotope is less than 2%, and more preferably less than 1% of the total isotope applied. For example, Hehrlein et al (1995) differentiate radioactive stents produced using ion implantation, the use of which they characterize within their study for medical applications, from a coated stent which they considered to be non-applicable and lacking medical utility due to the expected degree of leaching, especially if the medical device needs to flex in any manner. The idea being that a coating would simply flake off the surface of the device and possibly enter the circulatory system.

An alternate solution for treating the exterior of a device has also been proposed that involves electro-plating the device, for example with gold-198 (U.S. Pat. Nos. 5,059, 166; 5,167,617). This latter method applies to a limited range of isotopes and substrates that would be capable of being plated. It is, therefore well recognized within the art that present methods of coating devices with radioisotopes are deficient for the preparation of devices for use in radiotherapy.

There are many benefits associated with radiochemically coating devices. For example, the process is commercially scalable and allows for batch processing of high purity radioisotopes. Such a process combines uniform fixing and apyrogenic attributes for in vivo use, which is particularly important for high volume production. A large range of radioactivity and isotopes can be affixed uniformly, producing homogeneous coatings on a device and allowing customization of product. This process has a high utilization of isotopes, making it clean and efficient compared to other affixing methods. Furthermore, radiochemical coating of devices could utilize isotopes that are otherwise not available in devices prepared by ion implantation or transmutation methods. Similarly, a range of surfaces and non-metalic materials including synthetics, or other bio-compatible materials, could be coated with radioisotopes of interest for use. Thus there is a need to develop a simple method for preparing radioactively treated medical devices so that the radiochemical coating exhibits negligible or no leaching of the isotope in a test solution, or when implanted.

One study has examined the relative absorption of ions in dilute aqueous solutions on glass and plastic surfaces in order to determine the degree of contamination of these surfaces following their exposure to a range of isotopes (Eichholz et al 1965). The method employed adding the desired radioisotope to hard or distilled water and immersing the glass or plastic substrate within this solution for various lengths of time. Following a rinsing step using distilled water, the substrate was dried at 100° C. and the remaining radioactivity of the substrate determined. They note that increasing the concentration of ions in the water-isotope mixture reduced the contamination of isotope on the substrate surface, and that decreasing the pH of this mixture also reduced contaminaton. No methods are disclosed that attempt to optimize the coating of the substrates with a radioisotope, nor is there any suggestion or disclosure of the use of such a method for the preparation and use of an isotopically coated device. Furthermore, there is no teaching of how permanent the coating of the substrate is, nor is there any information as to the degree of leaching of the isotope from the coated substrate. Rather, Eichholz et al were interested in reducing or eliminating radioactive contamination of glassware, whereas the method of this invention is directed to producing a uniform distribution of radioisotope on the surface of a medical device, as well as maximizing the yield and permanently affixing the radioisotope on the surface of the medical device.

It has been observed that following the methods of this invention, coated devices can be produced with high yield, if this is desired, with the coating applied in a uniform manner. Furthermore, leaching of the isotope from the surface of the coated substrate is markedly reduced over other processes for coating a surface of a substrate, for example, that involve a step of heating to dryness in order to affix the radioisotope onto the surface of the device. Lastly, the methods of this invention are readily applied to batch processing of a device to be coated, ensuring that coated substrates are produced with consistent coatings both within and between batches. Since there is negligible leachate of the coated radioisotope from the coated device, the coated devices as described herein are well suited for use within medical applications where a localized therapeutic treatment is desired.

It is an object of the invention to overcome disadvantages of the prior art.

The above object is met by the combinations of features of the main claims, the sub-claims disclose further advantageous embodiments of the invention.

SUMMARY OF THE INVENTION

The present invention relates to a method of producing a uniform distribution of radioisotope on a surface of a device. Furthermore, this invention is directed to coated products prepared using the disclosed method. More specifically, this invention is directed at permanently affixing a radioisotope of interest on the surface of a medical device.

The present invention pertains to a radioactively coated medical device characterized in that leachate from the coated substrate is of less than about 1%. Preferably the leachate is of less than about 0.5%.

This invention also includes a radioactively coated medical device as defined above that is coated with a radioisotope selected from the group consisting of Y-90, Pd-103, Pd-112, Co-55, Co-57, Co-60, Ag-110, Ag-111, Ag-112, Ag-113, Au-199, Cu-64, Re-186, Re-188, Ir-192, Ir-194, Mo-99, Ni-63, In-111, Tc-99, P-32, P-33, C-14, S-35, Cl-36, I-125, I-131, I-123, I-124, At-211, Gr-68, Ho-166, Gd-159, Pm-142, Gd-153, Yb-169, Am-241, and Yb-60.

This invention is also directed to the radioctively coated medical device as defined above wherein the medical device can comprise a variety of surface geometries, and is selected from the group consisting of: stent, expandable stent, catheter, delivery wire, source for brachytherapy, brachytherapy seed, source for an after-loader, seed, wire, protheses, valves, sutures and staples or other wound closure device. If a stent, this invention pertains to stents further characterized in having an axial uniformity of less than about 20%, and a radial uniformity of about 20%.

The present invention embraces a method of treatment of a patient in need thereof, comprising administering the coated radioactive device as defined above. The coated radioactive device as defined above may also be used for the treatment of cell proliferation.

The present invention also provides a first method for coating a substate with a radioisotope comprising:

a) pre-coating the substrate by immersing a cleaned substrate within a seeding solution containing an acid and a non-radioactive metal, at a temperature of between 90 and 95° C. to produce a pre-coated substrate;

b) baking the precoated substrate at a temperature below the recrystallization temperature of the substrate;

c) immersing the precoated substrate within a matrix solution containing a $\gamma$, $\beta^+$, $\alpha$, $\beta^-$ or $\epsilon$, emitting metallic radioisotope with a valence of two, at a temperature of between 90 and 95° C. to produce a coated substrate;

d) baking the coated substrate at a temperature below the recrystallization temperature of the substrate;

The present invention relates to the above first method wherein the metallic radioisotope is selected from the group consisting of Y-90, Pd-103, Pd-112, Co-55, Co-57, Co-60, Ag-110, Ag-111, Ag-112, Ag-113, Pm-142, Am241, Gd-153, Gd-159, Yb-169, Ho-166, Au-199, Cu-64, Re-186, Re-188, Ir-192, Ir-194, Mo-99, Ni-63, In-111, and Tc-99m. Preferably the metallic radioisotope is Pd-103.

The present invention includes the above first method, wherein the matrix solution comprises a reducing agent and a stabilizing agent. For the coating of metallic Pd-103, preferably, the stabilizing agent is EDTA and the reducing agent is hydrazine sulfate, and the pH of the matrix solution is from about 7 to about 12.

This invention also pertains to the first method as defined above wherein the substrate is a medical device. Furthermore, the medical device can comprise a variety of surface geometries, and is selected from the group consisting of: stent, expandable stent, catheter, delivery wire, source for brachytherapy, brachytherapy seed, wire, seed, protheses, valves, and staples or other wound closure device. Preferably, the medical device is a stent, wire or seed. More preferably, the substrate is metallic. If metallic, preferably the substrate is stainless steel and nitinol.

The present invention is also directed to a medical device prepared using the first method as defined above, and to a method of treatment of a patient in need thereof, comprising administering the coated radioactive device.

The present invention also provides for a second method for coating a metallic medical device with a radioactive isotope comprising:

a) immersing the metallic medical device into an aqueous salt solution, at a pH of about 10 to about 12, and comprising a radioactive isotope, the metallic medical device acts as a first electrode;

b) inserting a second electrode with the aqueous salt solution;

c) applying a current to create a potential difference between the first and second electrodes;

d) removing the current, and rinsing the metallic medical device, allowing to air dry, and e) optionally, baking at a temperature below the recrystallization temperature of the substrate.

Preferably, the metallic medical device is a silver medical device, and the radioactive isotope is selected from the group consisting of S-35, Cl-36, Mo-99, I-123, I-124, I-125, I-129, I-131, Pd-103, Ho-166, Y-90, P-32 and Ce-144.

The present invention also includes the second method defined above, wherein the step of applying, comprises applying a current of from about 15 $\mu$A to 20 $\mu$A, for about 2 hours.

The present invention also pertains to a medical device made by the second method as defined above. The medical device may comprise a variety of surface geometries, and is selected from the group consisting of: stent, expandable stent, source for after-loader, source for brachytherapy, brachytherapy seed, delivery wire, catheter, seed, wire, protheses, valves, sutures, and staples or other wound closure device. Preferably, the medical device is a stent.

Substrates coated using the methods of this invention, are produced with a uniform coating, improving over methods that simply employ evaporating the radioisotope to dryness. Furthermore, these coated devices can be produced with a high yield of radioisotope, and exhibit negligible, industrially or medically acceptable, rates of leaching of coated radioisotope. Furthermore, the methods of this invention are readily used for batch processing substrates thereby ensuring that coated substrates are produced with consistent coatings both with and between batches.

This summary of the invention does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 10A shows a uniformly coated stent; FIG. 10B shows an unevenly coated stent with a greater loading of isotope on one end of the stent from the other; FIG. 10C shows another coated stent revealing a saddle shaped loading of radioisotope.

DESCRIPTION OF PREFERRED EMBODIMENT

Figure 1:
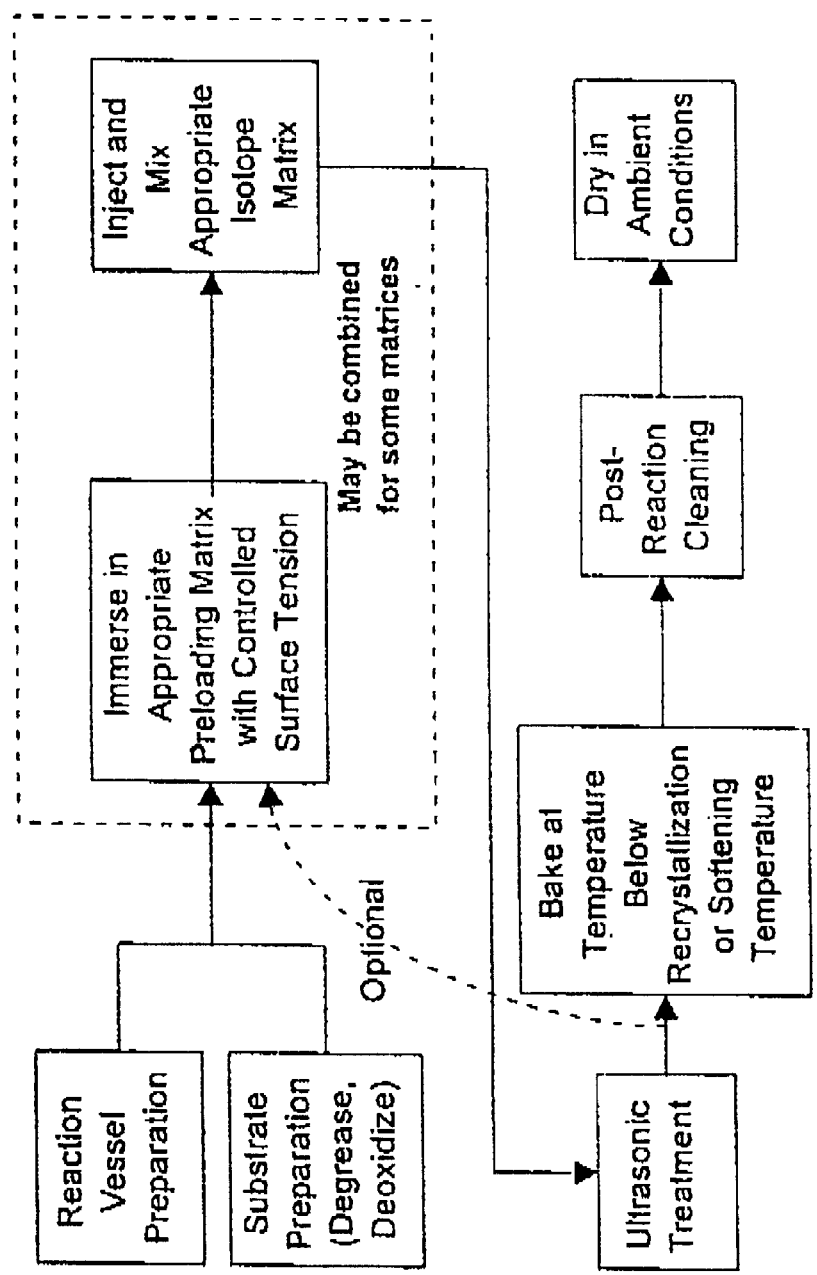
FIG. 1 outlines one of several possible methods of affixing radioisotopes onto medical devices.

This invention is directed to a radioactively coated substrate, and to methods for producing radioactive coatings on such substrates. More specifically, this invention embraces the coating of implantable medical devices such as stents, catheters, radioactive seeds and the like for use in medical treatments with at least one radioisotope of interest.

The following description is of a preferred embodiment by way of example only and without limitation to the combination of features necessary for carrying the invention into effect.

This invention provides methods for producing a radioactively coated substrate. This invention also provides for a radioactively coated substrate that exhibits low rates of radioisotope leaching. These low rates of leaching permit the use of the coated substrate within medical applications. Medical devices, implants, and other sources may be made radioactive using a radioisotope of interest, typically selected from γ, β$^+$, α, β$^-$ or ε (electron capture) emitting radioisotopes, or a combination thereof.

It is desired that a radioactive device suitable for a range of applications must exhibit a low rate of isotope leaching so that if, for example, the device is implanted or localized within a biological system, there is negligible leaching of the radioisotope from the coated substrate. It is generally considered that less than 5% of the total radioactivity may leach from a radioactively coated substrate within a define period of time. For coated medical devices that are implanted or used within a biological system, it is preferred that less than about 2% of the total radioisotope leach from the surface of the device. More preferably, a coated substrate useful for medical applications is characterized with less than about 1% of the total radioactivity that leaches off the coated substrate.

Due to these stringent requirements, it is generally held that radioactive medical devices suitable for internal use can not be prepared by applying a radioactive coating (e.g. Hehrlein et al. 1995; Fischell et al. 1996). However, the present invention provides coated substrates characterized by exhibiting low rates of leaching, for example less than about 2% of the total radioactivity coated onto the substrate, which are suitable for medical devices for use within biological systems and for internal use. Furthermore, the present invention provides several methods for the production of such coated substrates. While not to be considered limiting in any manner, below are outlined two methods for the production of radioactively coated substrates characterized as having a leach rate of less than about 2%. Such coated substrates may be used for a range of applications including but not limited to medical devices.

By "medical device" it is meant any apparatus that is used for the treatment of a medical ailment, and that can be treated in such a manner as to deliver ionizing radiation at a site requiring such treatment. The substrate of the medical device may be metallic or non-metallic in nature, as long as there is some affinity of the substrate for the radioactive chemical that is used for the coating process. Metallic substrates include, but are not limited to, aluminum, bronze, brass, copper, zinc, titanium, platinum, tantalum, palladium, stainless steel, zirconium, nitinol (nickel titanium alloy), and silver. Non-metallic substrates include, but are not limited to, plastics such as nylon, Teflon®, and the like, or other suitable polymeric materials, for example silicone, as well as plastic coated wire, enamel-coated glass, ceramic, and glass. With several of these substrates, slight modifications to the methods disclosed herein may be required in order to accommodate the protocol, as would be evident to one of skill in the art. Furthermore, expandable devices have been successfully loaded with radioisotopes using the method of this invention with the similar rates of leaching after changing the shape of the device, as non-expandable devices.

Typically the medical device is implanted, however, it may also be reversibly inserted within, and traverse the length of, an already implanted device such as a catheter (e.g. WO 93/04735, which is incorporated by reference). Furthermore, these devices may be applied on the exterior of a site requiring treatment should such a need arise. While not intended to be limiting in any manner, medical devices that may be coated using the methods of this invention may include stents, expandable stents, catheters, after-loader sources, or sources for braycheotherapy, seeds, protheses, needles, valves, staples, sutures or other wound closure devices as would be recognized by one of skill in the art. These devices may be of arbitrary shape and for any purpose, that requires the use of a radioactively treated medical device. Furthermore, it is contemplated that "medical device" also includes substrates that can be coated with a radioisotope of interest or combination thereof, and used as a radioactive source within encapsulated structures such as seeds (e.g. U.S. Pat. Nos. 5,163,896; 4,994,013; 4,815,449; 5,405,309; 4,702,228, which are incorporated by reference), delivery wires (e.g. U.S. Pat. No. 5,575,749) or the like as would be well known to one skilled within the art. These encapsulated structures are also considered to be medical devices.

Figure 6A:
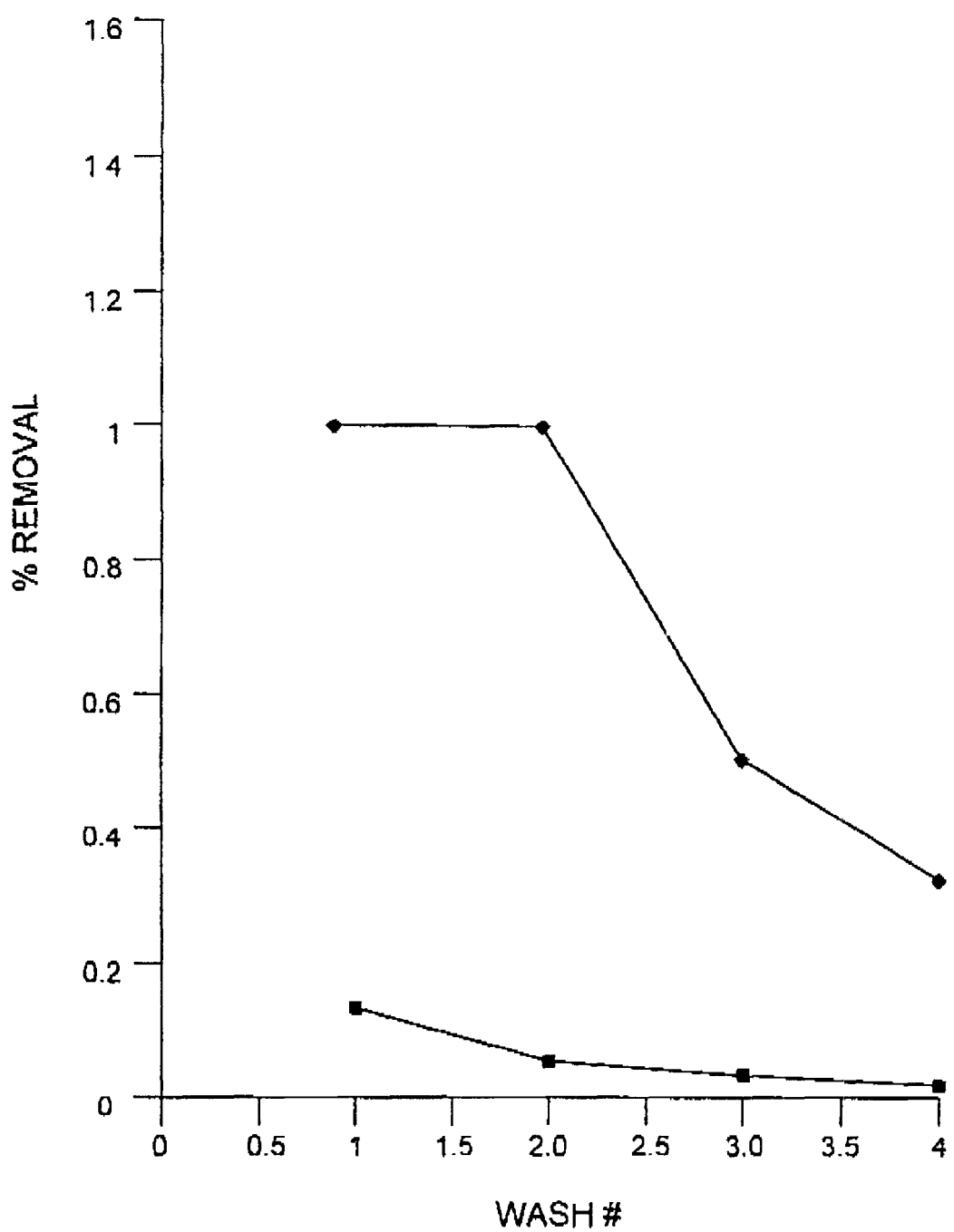
FIG. 6 shows a comparison between the rate of leaching of radioisotope from surfaces coated using Method A of this invention either involving the step of tuned vibrational cavitation (♦), or a step involving heat-evaporation (■) for either Y-90 (FIG. 6A), or P-32 (FIG. 6B).

By "coated medical device" it is meant a medical device that comprises a radioactive coating and exhibits a leach rate of less than about 2% of the total coated radioisotope. If the coated medical device is to be used directly for in vivo applications, then the rate of leaching of the radioisotope from the surface of the medical device, as determined by sampling of the rinsing solution after 15 minute ultrasonic leaching in normal saline at 37° C., should be less than about 1%, preferably less than about 0.1% of the total amount applied. It is to be understood that using the methods of the present invention, leach rates of less than about 0.05% have been obtained. Coated medical devices, such as stainless steel stents, have repeatedly been produced by the processes as described herein, for example but not limited to Method A as described below, with removable contamination levels on the final leaching test of less than 0.01% using Y-90 (see FIG. 6A), or P-32 (e.g. Tables 2 and 3, Example 2). Similarly, devices coated with Pd-103 103 (e.g. Tables 4 to 8, Example 3) or In-111 or In-111 (Table 9, Example 3) have been produced using Method B, as described below, that are characterized as having leach rates from about 1% to about 0.05% or less (see Tables 4 to 8 of Example 3). However, it is also contemplated that coated medical devices produced using the methods as described herein may also be encapsulated in some manner as is known within the art, in the form of a seed. In this application, the coated device may not require the same stringent degree of leaching as desired for coated medical devices that are used for direct implantation applications. The present invention also pertains to expandable coated medical devices, for example but not limited to a coated expandable stent. Using the methods described herein, it has been observed that a conformational change of the coated substrate may occur with negligible increase in leachate (see Table 9, Example 3).

By "temperature below the recrystallization, or softening temperature of the material comprising the medical device" it is meant a temperature that does not alter the physical properties of the medical device so as to affect the function or other desired characteristic of the medical device. Any selected temperature must also not adversely effect the properties of the selected radioisotope. This temperature may reach 1,500° C. or more depending upon the substrate being coated. For example, radioactively coated glass has been baked above the melting temperature of glass without adverse effects on the substrate-isotope coating. Typically the maximum baking temperature will be determined by the substrate of the medical device, rather than the radioisotope used for coating. Temperatures contemplated for baking the coated medical device include from about 100° to about 1,500° C., and typically range from about 200° to about 600° C., more preferably from about 250° to about 450° C., depending upon the method used. Without wishing to be bound by theory, this step aids in the curing of the coated radioisotope with the surface of the substrate of the medical device and helps ensure the formation of bonds between the isotope and surface of the medical device.

Tuned Vibrational Cavitation Method for Coating Substrates (Method A)

The radioisotopes of the following list, while not to be considered as limiting, may be used in accordance with method A of the present invention:

Non-metallic: P-32, P-33, C-14, S-35, Cl-36, I-125, I-131, I-123, I-124, At-211, Metallic: Y-90, Pd-103, Pd-112, Co-55, Co-57, Co-60, Ag-110, Ag-111, Ag-112, Ag-113, Au-199, Cu-64, Re-186, Re-188, Ir-192, Ir-194, Mo-99, Ni-63, In-111, Tc-99m, Gr-68

Rare earths: Ho-166, Gd-159, Pm-142, Gd-153, Yb-169,

Actinides: Am-241 preferably wherein the radioisotope is selected from P-32, Y-90, Ag-110, Ag-111, Ag-112 or Ag-113, and more preferably wherein the isotope is P-32 or Y-90.

It is also contemplated that mixtures of any of the above isotopes may also be used with method A of this invention so that medical devices coated with several isotopes capable of emitting a range of radiation doses (i.e. varying strengths of ionizing radiation), or for varying lengths of time may be produced By "immersion matrix" it is meant the solution that the substrate, for example, a medical device is placed within before, or during, the coating procedure. The immersion matrix may comprise a range of ingredients directed at increasing the affinity of the surface of the medical device to receive a radioisotope of interest, or the immersion matrix may also be selected to enhance the coating of the medical device with the selected radioisotope of interest, or both. The immersion matrix may also be selected to help drive the radioisotope from the solution and onto the surface of the medical device.

Without wishing to limit the compositions that the immersion matrix may comprise in any manner, it is contemplated that the immersion matrix in method A may consist of water, or water containing a salt or combination of salts, and optionally a buffer, or the immersion matrix may comprise other reagents such as an alcohol. However, the immersion matrix may comprise other ingredients as deemed necessary. The composition of the immersion matrix can comprise any ingredient which is capable of being safely used for tuned vibrational cavitation providing it does not chemically react in an aggressive fashion with either the substrate or radiochemical. It has been noted that in some instances the addition of salt is more effective in enhancing the yield of coated isotope than water alone, however, the selection of other compositions may also prove effective for increasing overall yield. If a salt is selected as a component of the immersion matrix, a range of concentrations maybe used in order to enhance the coating of the medical device. Without wishing to be limiting in any manner, a range of salt concentrations from about 0.05 to 20% (w/v) is contemplated, or more preferably with a range from about 0.1 to 5% (w/v). It has also been observed that the use of ultra pure chemicals aids in the coating process.

Figure 2:
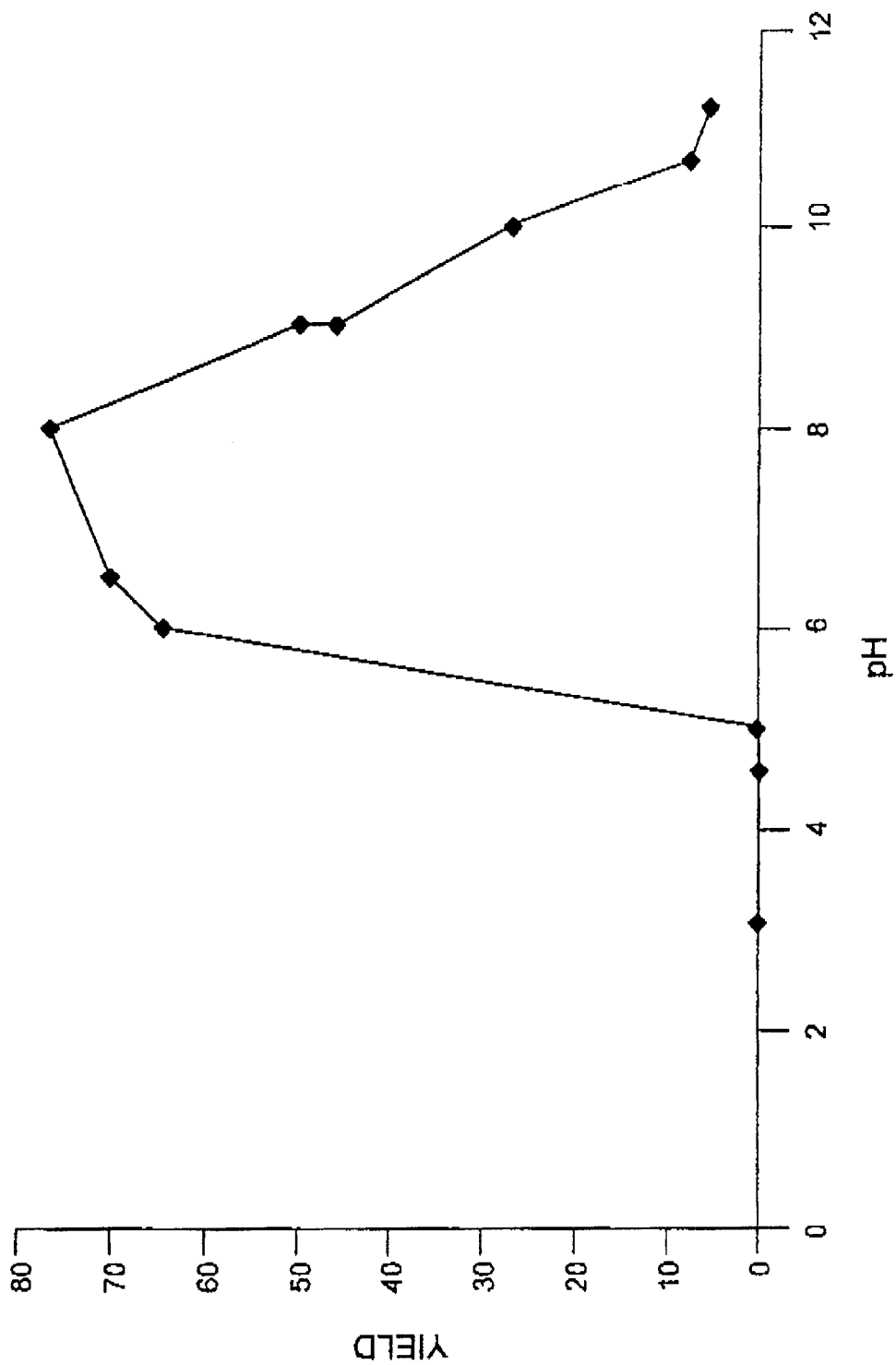
FIG. 2 shows the effect of pH on the yield of a stainless steel stent coated with Y-90 using Method A as described herein.

It is also contemplated that the pH of the immersion matrix is selected to increase the efficiency of the coating process. A range of pH may be used, however an embodiment of method A utilizes a range from about pH 4.0 to 11 and will depend upon the radioisotope used. For example, for Y-90 an effective range of pH is between from about pH 5.5 to 10.5 (see FIG. 2).

The immersion matrix may also comprise agents to alter the surface tension of the solution. For example, without wishing to limit the selection of such agents in any manner, an agent may include ionic or non-ionic detergents, or alcohol.

Figure 3:
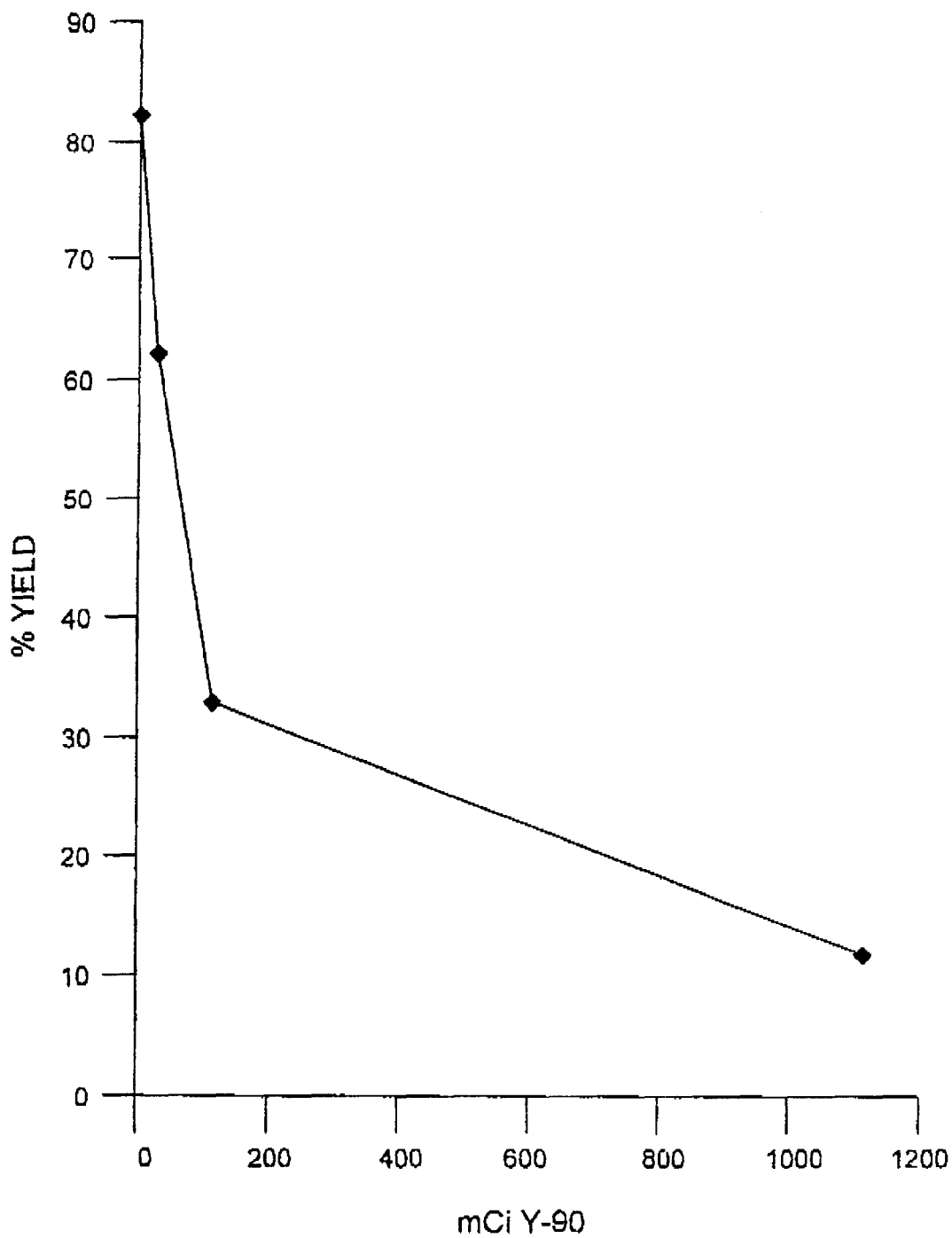
FIG. 3 shows the percent of radioactivity (of the total isotope added to the immersion matrix) adsorbed onto the surface of a stainless steel stent over a range of concentrations of radioisotope present within the immersion matrix (using Method A as described herein). With increasing radioisotope concentration, the percent of radioactivity (i.e. % yield) decreases, however, the amount of radioisotope coating the substrate (not shown in this figure) increases. The isotope used in this analysis is Y-90.

By "yield" it is meant the amount of radioisotope remaining on the surface of the medical device or substrate as prepared using the method of this invention. The yield is determined from the amount of radioisotope added to the immersion matrix. Following method A, yields of about 80% have been routinely obtained. This value is to be compared with the method of Eichholz et al, which produce coated substrates with yields of about 5% (see below). Typically a higher amount of radioisotope coating can be obtained by adding more radioisotope to the immersion matrix, however, the yield decreases with increased concentration of isotope within the immersion matrix (FIG. 3). Even though yields of 80% can be routinely obtained, more uniform coatings of the substrate are observed with yields of about 40–60%.

It has been observed that very low rates of leaching are detected, following method A of this invention, irrespective of the yield. That is to say, that acceptable rates of leaching of an isotope from a coated substrate are obtained using the method of this invention whether the yield is from about 40–60%, or 80%.

Typically, the medical device is immersed within the immersion matrix prior to the addition of the radioisotope of interest. The isotope is then added to the immersion matrix, without exchange of the immersion matrix. However, it is contemplated that more than one immersion matrix may be used for the coating process and that the medical device could be placed within one or more immersion matrix solutions prior to exposure to an immersion matrix comprising a radioisotope of interest.

By "tuned vibrational cavitation" it is meant any method of activating the immersion matrix so as to form bubbles of various sizes and states within the immersion matrix that are capable of collapsing thereby imparting shockwaves within the immersion matrix to help drive the isotope onto the surface of the medical device. Tuned vibrational cavitation may impart a range of shockwave forms to the immersion matrix. It has been observed that square or sinusoidal wave forms can be effectively used in the method of this invention. However, tuned vibrational cavitation comprising wave functions of a variety of forms, frequencies, amplitudes, or complexities, or mixtures of frequencies, amplitudes or wave forms, that aid in driving the isotope of interest onto the surface of the medical device, can be used with the method of this invention. Examples of eliciting tuned vibrational cavitation include, but are not limited to, laser tuning (which can be used vibrate and excite molecules e.g. Wizemann et al 1997; Arlinghaus et al 1997) microwave or ultrasonic treatments of the immersion matrix. However, other means of imparting shockwaves within the immersion matrix may also be used, for example high temperature, modified pressure etc. If ultrasonic treatment is employed as a source of tuned vibrational cavitation, then a square wave function may be selected for the coating step, as such wave forms have been observed to enhance the coating of the medical device. Without wishing to be bound by any theory, shockwaves produced using a square wave function, impart to the immersion matrix, and the radioisotope of interest, a higher energy when compared with shockwaves produced by sinusoidal waves. Sinusoidal waves may be useful in the rinse stages of the coating method of this invention. However, there may be applications where sinusoidal wave functions may be employed to coat the medical device. As an example, an immersion matrix that comprises a mild buffering solution maintaining pH at about 8, and 1% saline, an ultrasonic treatment of 10 min has proved sufficient for producing a high yield coating (>80%) on stainless steel stents with Y-90.

Figure 4:
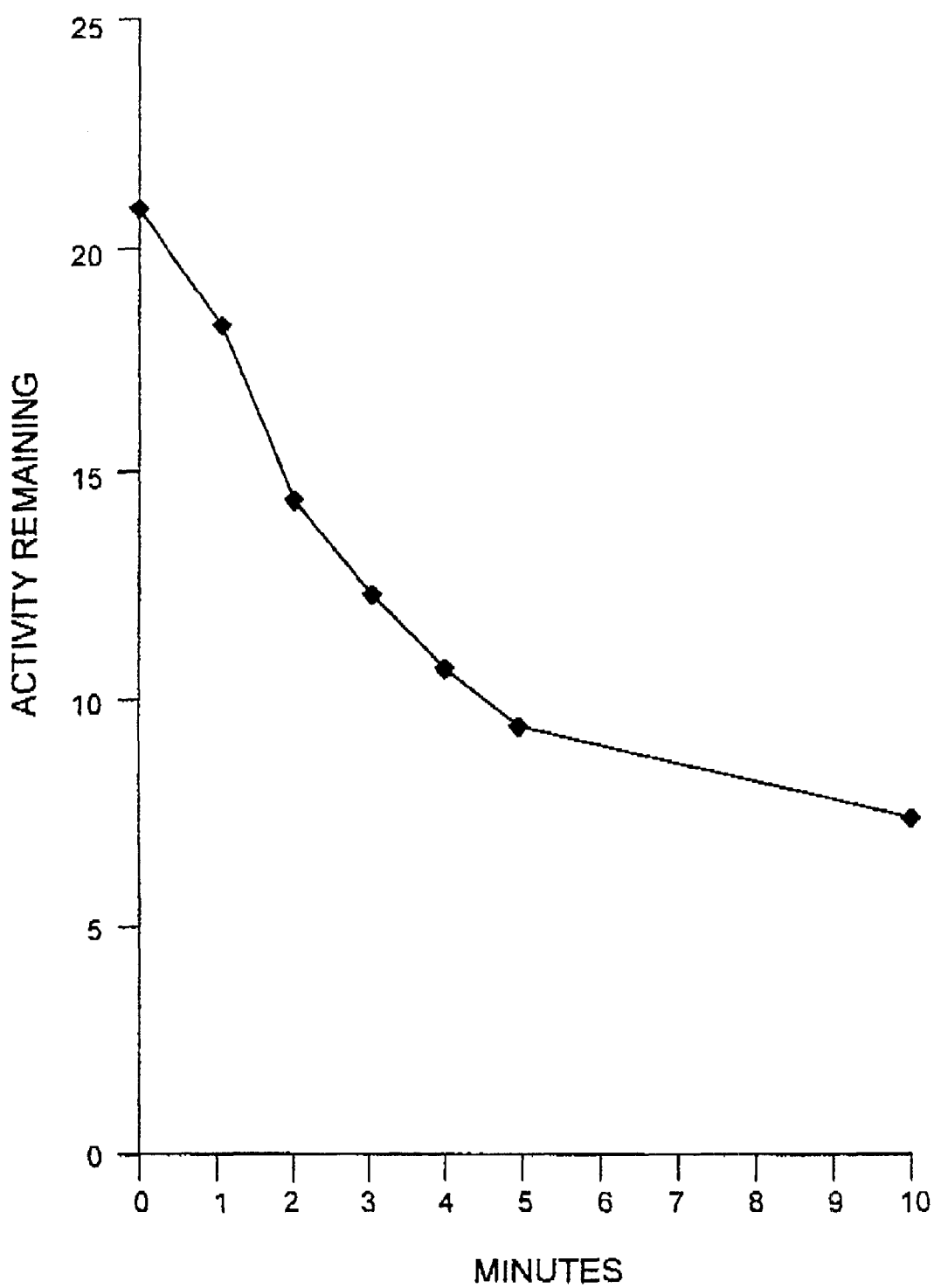
FIG. 4 shows the rate of removal of radioisotope from the immersion matrix as it is deposited onto the surface of the substrate being coated during the step of tuned vibrational cavitation using Method A as described herein. The data is for a 15 mm stainless steel stent immersed in 1% NaCl, 0.1% NaHCO$_3$ ultrasonic treatment, coated with Y-90.

Typically the substrate to be coated is exposed to tuned vibrational cavitation, in the presence of radioisotope, from about 5 min to 3 hours, depending upon the coating desired on the substrate. It has been found that varying the time of the ultrasonic step is one variable that effects the yield of the coated substrate. However, this time variable may have less impact on yield if the appropriate immersion matrix is selected, since high yields have been observed with short (5–10 min) exposures to tuned vibrational cavitation. The rate of the coating procedure can be monitered during the step of tuned vibrational cavitation. For example, FIG. 4 shows the rate of removal of a radioactive isotope from the immersion matrix during ultrasonic treatment as it is deposited onto the surface of the immersed device.

Figure 10:
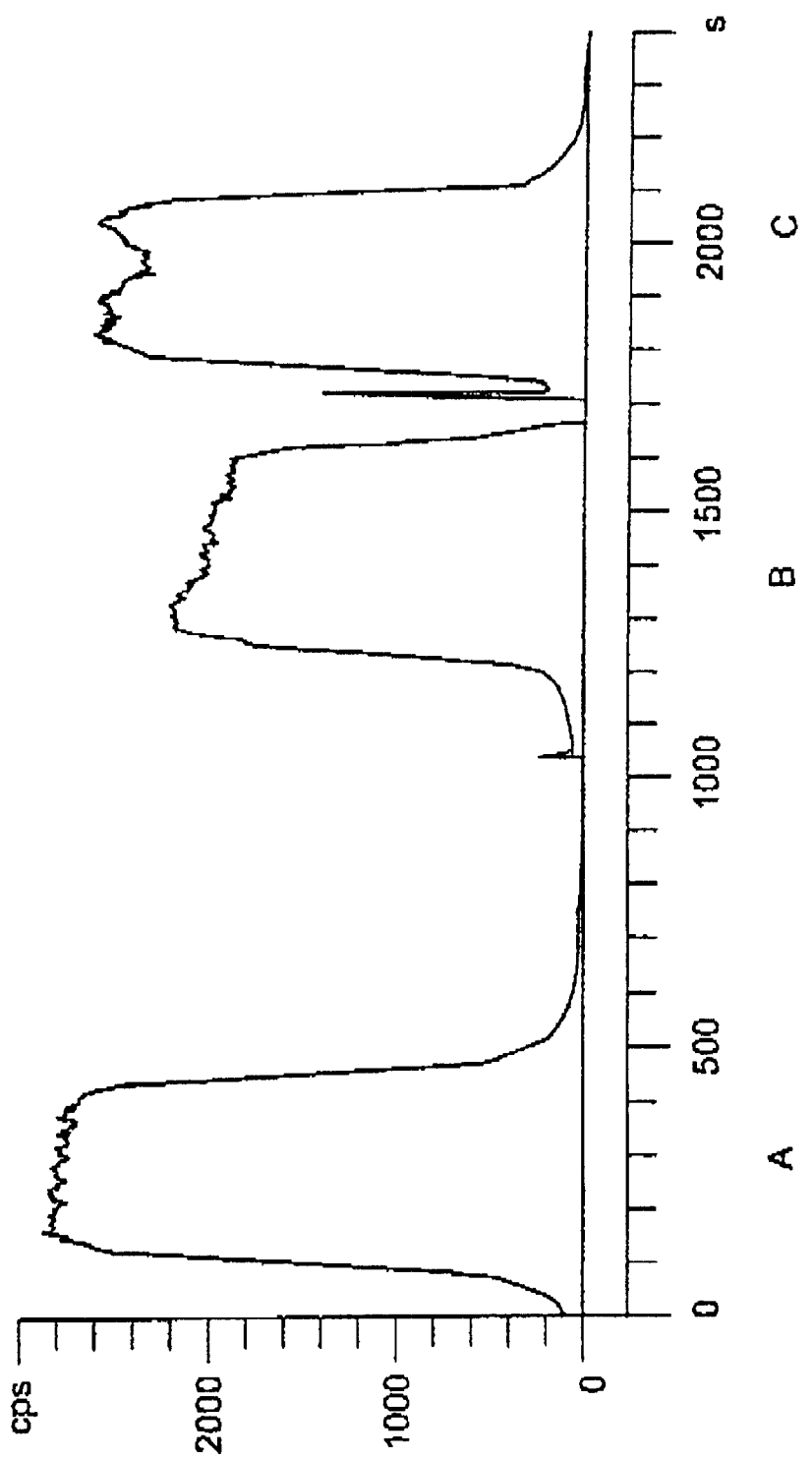
FIG. 10 shows three separate longitudinal uniformity scans for three coated stents.

There is a relationship between the rate of deposition of a substate being coated using tuned vibrational cavitation, and the uniformity of coating along the length of the stent. For example, it has been observed that both longitudinal and vadial uniformity (defined below) increases with slower deposition rate. However, by using higher rate of deposition, saddle-shaped stent coatings can be obtained (e.g. see FIG. 10C). It is contemplated that a stent coated in this manner may have applications if it is desired that the ends of the stent incorporate higher radioisotope loadings. The rate of deposition is affected by the pH and temperature of the solution, as well as by the surface area (of the substrate) to volume (of the solution) ratio, and the intensity of the ultrasonic treatment. Without wishing to limit the method of this invention in any manner, we have found that uniform coatings on stents, with yields in the order of 40%, can be obtained by using a 15 mm stent:2 ml vol of immersion matrix ratio, at pH 6, and incubating at 50° C. with 10 min of ultrasonic treatment.

Following method A of this invention a distinct improvement is observed in the rate of leaching of a radioisotope from the surface of a coated substrate when compared with other coating techniques (such as those derived, for example, from Eichholz et al, 1965). For example, if the step of "loading" the isotope onto the surface of the substrate, using tuned vibrational cavitation is replaced with a step involving heating the substrate (after exposure to the immersion matrix for equivalent lengths of time) at 200° C. to dryness, a marked increase in the leaching rate is noted (see FIGS. 6A, for Y-90, and 6B, for P-32).

Figure 5:
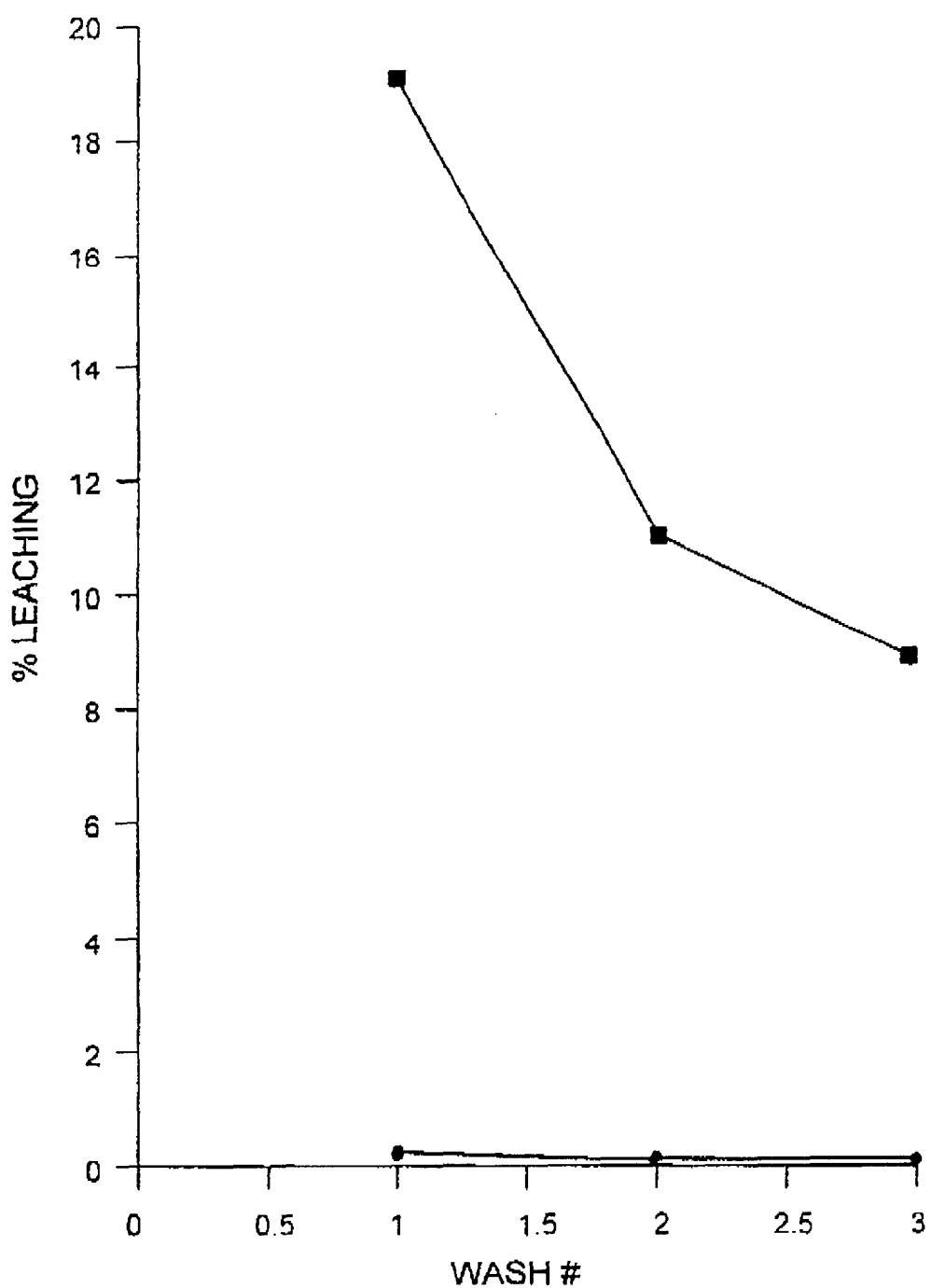
FIG. 5 shows a comparison in the rate of leaching between a stent baked for 30 min at 300° C. (♦), and a non-baked stent (■), when coated with Y-90, using Method A as described herein.

Following tuned vibration cavitation, the substrate is baked at a temperature below the recrystallization or softening temperature of the substrate. The maximum baking temperature will be determined by the substrate of the medical device, rather than the radioisotope used for coating. Temperatures contemplated for baking the coated medical device include from about 150° to about 1,500° C., and typically range from about 200° to about 600° C., more preferably from about 250° to about 450° C. A comparison of the rate of leaching of stents coated using the method of this invention, but differing with respect to the use of the baking step can be seen in FIG. 5.

With reference to FIG. 1, there is outlined one aspect of an embodiment of method A of this invention. Typically the method A involves:

1) preparing the reaction vessel used for coating the medical device, as well as the medical device itself prior to initiating the coating procedure. The purpose of this step is to expose the maximum amount of the surface of the substrate to the coating process by removing any impurities. Any method of treatment of the reaction vessel or medical device may be included within this step ensuring compatibility between the substrate and cleaning material. This treatment may include degreasing and/or deoxidizing the surface of the vessel, and medical device as indicated within FIG. 1. Suitable compositions for such treatment include, but are not limited to nitric, citric, or chromic acids. Ideally, the selected cleaning material is to be adopted to the substrate being coated, and such selections are know to those skilled in the art;

2) immersing the medical device in the appropriate immersion matrix;

3) adding the isotope of interest to the immersion matrix;

4) exposing the immersed medical device to tuned vibrational cavitation for a period of time to sufficiently drive the isotope of interest onto the surface of the medical device. This step may take place at a temperature that significantly deviates from ambient temperature in order to optimize coating of the medical device;

5) optionally re-immersing the medical device in a new immersion matrix. The new immersion may comprise more of the same radioactive isotope as in the initial immersion matrix, or may comprise a new immersion matrix composition comprising an alternate radioisotope and repeating the exposure to tuned vibrational cavitation;

6) rinsing the coated device in water and baking at a temperature below the recrystallization, or softening temperature of the material comprising the medical device;

7) rinsing the medical device to remove radioisotope not permanently affixed to the surface of the medical device. The rinsing solution may be the same or different as the immersion matrix. This step optionally includes the use of tuned vibrational cavitation and may be repeated as needed in order to produce a coated medical device with minimal or no leaching of the radioisotope; and 8) drying the device.

By "uniformity" of the coated surface it is meant the consistency of radioactive emission detectable along the length (longitudinal uniformity), and optionally, depending upon the shape of the substrate being coated, uniformity may also be determined in a second dimension. For example with stents, routine uniformity analysis involves assessment of the longitudinal uniformity (see FIGS. 9 and 10), as well as radial uniformity (see FIG. 8).

The level of radioactivity of the coated medical device can be tailored to achieve a range of therapeutic doses by varying the amount supplied to the immersion matrix.

It is to be recognized that the use of specific chemicals within the immersion matrix or rinsing solutions, temperatures of exposing the medical device during tuned vibrational cavitation, seeding, electroless plating, baking or rinsing, and the duration of each of these steps, can be modified and will be a function of the radioisotope, the substrate material of the medical device as well as the geometry of the medical device that is being coated. The above processes are to be considered a guide to the conditions used to obtain a coated medical device.

There are major differences between the methods outlined above to those disclosed by Eichholz et al (1965). The affixing process of this invention produces substantially different results from the process described in Eichholz et al. This difference is highlighted by the fact that coated substrates prepared using the method of Eichholz et al result in coating efficiencies of 5% of the initially added radioisotope to the immersion matrix. However, coating efficiencies obtained using the methods of this invention produce coated substrates yielding greater than 70% efficiencies, and routinely substrates are prepared comprising about 80% of the radioisotope added to the immersion matrix. Furthermore, substantial rates of leaching (e.g. above 0.2%) of the coated substrate produced by the method of Eichholz et al are observed after 3 or more rinsing steps, however, as indicated above, rates of leaching of less than 0.05% are produced by method A of this invention.

The differences between the methods of this invention and that of Eichholz et al that produce coated substrates with such differing properties include:

a) Choosing the appropriate immersion matrix is important in obtaining a coated substrate with uniform distribution and high yield of isotope. Using the processes described herein, radioactive P-32, Y-90 and Pd-103 substrate coatings on stents have routinely achieved longitudinal uniformities of at least ±15%, and radial uniformities of at least ±10%. Eichholz et al disclose that the use of hard water or salt dramatically reduces radioactive contamination of glassware. For example, Eichholtz et al report that the addition of 0.2% (w/v; equivalent to 0.02N) $CaCl_2$ was effective in abolishing the adsorption of Cs-137 on glass (e.g. see FIG. 2 of Eichholz et al). However, using the method A of this invention, the addition of salt (from about 0.05 to 20% (w/v), or from about 0.1 to 5% (w/v), or more preferably from about 0.5 to 3% (w/v)) and buffer (an amount sufficient to maintain the desired pH) has been found to dramatically increase the yield of the coating of radioisotopes of interest. Using 1% saline as the immersion matrix, at a pH of 7–10, yields of coated substrates in the order of 70% are routinely obtained. Furthermore, the addition of a buffer to the saline immersion matrix increased yields of about 90%. Therefore, according to the method A of this invention, selection of appropriate salt and buffer compositions will be important in achieving high coating efficiencies. However, it is to be noted that even in the absence of any added salt or buffer within the immersion matrix, yields of about 35% are obtained using method A of this invention and water (depending upon the pH of the water).

b) The use of tuned vibrational cavitation has been observed to dramatically increase the yield of isotope on the surface of a substrate prepared using method A of this invention. It has been observed that while the method of Eichholz et al results in yields on a rinsed coated surface (such as stainless steel) of 5%, when the same substrate is prepared with water as the immersion matrix, by adding the step of tuned vibrational cavitation and other steps of this method being kept constant, yields of at least 35% are routinely observed. Without wishing to be bound by theory, it is thought that the step of tuned vibrational cavitation enhances nucleation, that is this step is thought to enhance precipitation of the radioisotope onto the surface of the substrate.

c) The baking step also increases the adherence of the radioisotope to the substrate. In comparison, the 100° C. baking step of Eichholz et al is used to increase the rate of drying of the glassware under test and no parameters are disclosed to produce or test permanently affixed coatings. Without a baking step, leaching of the coating is enhanced in a saline rinse solution. For the process of method A described herein, yields greater than 35% have been routinely achieved using water as the immersion matrix, after rinsing radioactively coated substrates in an ultrasonic bath following a baking step. Without wishing to be bound by theory, it is proposed that high baking temperatures provide energy to allow the radioactive molecules to enter the substrate molecular structure to form chemical bonds as well as promote oxide layer formation. Both of these properties (forming bonds with the substrate and promoting oxide layer) enhance the yield and coating efficiencies of the method of this invention by ensuring that the coated radioisotope remains affixed to the substrate. In general it has been observed that while tuned vibrational cavitation and seeded electroless plating increase the amount of radioisotope that is able to coat and penetrate the substrate, baking ensures that the isotope coating bonds to the substrate.

Electroless Plating Method for Coating a Substrate (Method B)

The following method is used to produce a substrate coated with a radioisotope of interest, generally characterized as having a low specific activity. This method results in the production of a relatively thick layer of the radioisotope on the substrate surface. This is very different from the coating produced by method A outlined above which utilises radioisotopes of high specific activity, and produces coated substrates having a negligible dimension to the coating. Method B involves the plating of a substrate with a metallic radioisotope of interest using an electroless plating method. The coating produced using this latter method has a substantial thickness, and therefore the use of ultrasonic treatment is in general to be avoided as it may lead to a weakening of the coating. However, brief periods of ultrasonic treatment may be performed as required, for example to test the substrate for leachate.

Some commercially available radioisotopes have very low specific activities. In such cases the amount of radioisotope that must be coated on a substrate to provide adequate level of radiation, for the device to have medical utility, is high. Thick coatings are not achievable by the method of tuned vibrational cavitation. The method of electroless plating provides thick coatings however methods of the prior art, for example U.S. Pat. No. 2,915,406 also produces unacceptable levels of leaching. Consequently there is a need in the art for a coating method that allows the formation of a thick, uniform coat of radioisotope on a substrate which exhibits low level of leaching. The present invention provides a method B for producing uniformly coated substrates with enough radioisotopes of low specific activity to generate adequate levels of radiation and yet exhibit very low rates of leaching.

Preferably, the metallic radioisotope of interest for method B comprises a valence of two. Examples of suitable elements, which is not to be considered limiting, whose radioactive isotopes, may be used in accordance with method B of this invention are provided below:

nickel, gold, copper, molybdenum, tin, cobalt, iridium, rhodium, rhenium, tungsten, iron, boron, ruthenium, palladium, zinc, cadmium, chromium, lead, indium, silver, mercury, osmium, technetium, gallium, antimony, bismuth, arsenic, gaddiniumn, ytterbium, asaltine, iodine, phosphorus, germanium, silicon, vanadium, niobium, scandium, yttrium, strontium, barium, cesium, rubidium, sodium, potassium, barium, thulium, tantalum, selenium, potassium, samarium, magnesium, lithium, holmium, calcium, bismuth. For example, Y-90, Pd-103, Pd-112, Co-55, Co-57, Co-60, Ag-110, Ag-111, Ag-112, Ag-113, Au-199, Cu-64, Re-186, Re-188, Ir-192, Ir-194, Mo-99, Ni-63, In-111, Tc-99m, Gd-153, Yb-160, Ge-68, P-32, I-125.

The metallic elements in groups I, II and III listed above might require additional protection to provide good leaching results, since these elements are generally highly reactive.

It is also contemplated that mixtures of any of the above isotopes may also be used with method B of this invention so that substrates coated with one or more isotopes, capable of emitting a range of radiation doses (i.e. varying strengths of ionizing radiation) or for varying lengths of time, may be produced.

A substrate coated by a radioactive isotope of the above listed elements may also be further sealed using methods as known in the art, for example but not limited to those disclosed in U.S. Pat. Nos. 4,815,449; 4,994,013; 5,342,283; and 5,405,309 (which are incorporated by reference). Such additional coating may involve polymeric, ceramic, or metallic coatings. Preferably the secondary coating is selected from a bio-compatible material if it is to be used within a biological system.

Briefly, after preparation of the substrate surface, for example, cleaning or degreasing the surface, method B optionally comprises a seeding step where the substrate is pre-coated with a non-radioactive metal which is the same metal as that to be used for the radioactive coating. The seeding step provides a suitable surface upon which the radioactive metal may be deposited. Without wishing to be bound by theory, it is thought that the seeding step plays a role similar to tuned vibrational cavitation of method A. That is to say, it enhances nucleation. An example of a substrate that is coated using electroless plating with seeding is provided in Example 3 (electroless plating with seeding). However, such a seeding step is not always required. An example for electroless plating in the absence of a seeding step is provide in Example 3 (electroless plating without seeding).

After the step of seeding, followed by a brief rinse, the initial coating is hardened onto the substrate by baking the substrate at a temperature below the recrystallization or softening temperature of the substrate, for example, but not limited to, from about 80° to about 600° C. Following an optional wash, the pre-coated substrate is placed into a matrix solution and is subject to electroless plating where the radioisotope of interest is deposited onto the surface of the substrate. Typically the step of electroless plating occurs at an elevated temperature, for example above 80° C., and more preferably from about 90° to about 95° C. Following a brief rinse, the substrate is again baked at a temperature below the recrystallization temperature of the substrate, for example, but not limited to, from about 100° to about 600° in order to harden the coating.

If the substrate is coated in the absence of seeding, then following a step of cleaning, the substrate is immersed into a matrix solution and is subject to electroless plating where the radioisotope of interest is deposited onto the surface of the substrate. The step of electroless plating occurs at an elevated temperature, for example above 80° C., and more preferably from about 90° to about 95° C. Following a brief rinse, the substrate is again baked at a temperature below the recrystallization temperature of the substrate, for example, but not limited to, from about 100° to about 600° in order to harden the coating.

Radioactively coated substrates, prepared with or without the seeding step, may further be overcoated with a non-radioisotope counterpart of the metal used in the step of electroless plating. For example which is not to be considered limiting in any manner, a substrate coated with Pd-103 may be overcoated with inactive Pd. However, overcoating with a second metal may also be carried out providing that the two metals are compatible with each other. The overcoating procedure may comprise a step of electroless plating, occurring at an elevated temperature, for example above 80° C., and more preferably from about 90° to about 95° C. Following a brief rinse, the substrate is again baked at a temperature below the recrystallization temperature of the substrate, for example, but not limited to, from about 100° to about 600° in order to harden the coating. This second electroless plating step as just described may be repeated from about 1 to about 5 or more times as required. It has been observed that repeating the overcoating step reduces the leach rate of the coated substrate (see Example 3). It is to be understood that other methods for overcoating may also be employed including electroplating (as described herein Method C).

Substrates coated by this method (method B) are visually inspected, tested for leaching, and optionally tested for uniformity of the radioactive coating. By uniformity, it is meant the consistency of radioactive emission detectable along the length (longitudinal uniformity), and optionally, depending upon the shape of the substrate being coated, uniformity may also be determined in a second dimension. For example with stents, routine uniformity analysis involves assessment of the longitudinal uniformity (see FIGS. 9 and 10), as well as radial uniformity (see FIG. 8). Generally it has been observed that uniformity increases, as does the adhesion of the metallic radioisotope to the substrate, with increased concentration of the radioisotope coated onto the substrate.

By "matrix solution" it is meant the solution that the substrate is placed within in order to carry out electroless plating of the radioisotope of interest onto the substrate. Preferably the matrix solution comprises a salt or base suitable for dissolving the metal radioisotope of interest that is to be coated onto the substrate. For example, which is not to be considered limiting in any manner, for Pd-103, the matrix solution comprises may comprise $NH_4OH$. A stabilizing agent, for example, but not limited to a chelating compound, may also be added to ensure that the solute is maintained at a required concentration within the matrix solution. For example EDTA or EGTA may be used for this purpose. Preferably the chelating compound is EDTA. An electrolyte is also added to the matrix solution to drive the electroless plating process. Such electrolytes are known within the art (e.g. U.S. Pat. No. 2,915,406, which is incorporated herein by reference) and may include In the case of plating Pd-103, the preferred electrolyte is hydrazine sulfate. However, the matrix solution may comprise other ingredients as deemed necessary.

It is also contemplated that the pH of the solution used during the seeding step of method B, the seeding solution, is selected to increase the efficiency of the seeding process. A range of pH may be used, for example, from about pH 2 to 7 may be used, and will depend upon the radioisotope used. Similarly, the pH of the matrix solution of the electroless plating step of method B is also selected to increase the efficiency of the coating process. A range of pH maybe used, for example, but not limited to a range from about pH 7 to 12 and will depend on the radioisotope used.

The substrate is typically immersed in the seeding solution for 15 to 30 minutes and in the matrix solution for 30 to 90 minutes. However, depending on the radioisotope and the temperature of incubation these times may vary to maximize the yield and minimize the leaching.

In method B it is also contemplated that if the substrate is seeded, then the element used to seed the substrate may, or may not be, the same as the radioactive element used in the coating step. Furthermore, the seeded and coated substrate may be further overcoated as described above, with a non-radioactive metal that is the same or different to the radioactive metal used to coat the substrate. The overcoated metal may be applied using electroless, or electroplating, as required.

Preferably the substrate used for method B is metallic, however, any substrate may be used provided it can either be seeded with elements that will permit coating with the radioisotope of interest, or be overcoated with a metal as described above. Metallic substrates may include but are not limited to, aluminum, brass, bronze, zinc, titanium, platinum, tantalum, palladium, stainless steel, zirconium, nitinol, silver. Coatings have also been produced, on non-metallic substrates including plastics, silicone, ceramic, enamel coated substrates, for example enamel-coated glass, and glass. It is to be understood that the method (B) as described herein, may need to be optimized depending upon the substrate selected for the coating process in order to achieve a leaching rate suitable for medical applications. However, the general principles as disclosed may be followed in order to obtain metallic or non-metallic substrates coated with a radioactive isotope.

It has been observed that the yield, using method B, is higher when the temperature of the solution, at the seeding step, if used, the seeding solution, if used, and of the matrix solution, is maintained near the boiling point of water. Although a coating can be obtained at lower temperatures, the preferred range for both the seeding and the coating steps is between about 90 to 95° C. and most preferably about 92 to 95° C. At these temperatures, and following the method outlined below, yields routinely exceed 90%. Furthermore with the temperature ranges specified above it has also been observed that leach rate is very low, for example less than about 1%, and such coated substrates are acceptable for use as medical devices. Typically the leach rate of substrates coated using method B is below 0.1%. It has been observed that the degree of leaching increases above 2% and is commercially unacceptable if the seeding and electroless plating steps are performed at temperatures below 90° C.

Typically the method B involves (with a seeding step):

1) preparing the surface of the substrate, for example a medical device, prior to initiating the coating procedure. The purpose of this step is to expose the maximum amount of the surface of the substrate to the coating process by removing any impurities. Any method of treatment of the reaction vessel or medical device may be included within this step ensuring compatibility between the substrate and cleaning material. This treatment may include degreasing and/or deoxidizing the surface of the substrate. Suitable compositions for such treatment include, but are not limited to organic solvents, weak acids, or a combination thereof. Ideally, the selected cleaning material is to be adapted to the substrate being coated, and such selections are know to those skilled in the art. Without wishing to be limiting, the organic solvent may be acetone and the acid may be a mild organic acid for example from about 0.1% to about 10% ascorbic acid, preferably from about 0.5% to about 5% ascorbic acid. A dramatic decrease in the rate of leaching has been observed using a stainless steel substrate subjected to an acetone cleaning (Table 4, Example 3). Optionally, this step may include exposing the substrate to sonication at a temperature above room temperature to facilitate the removal of impurities, for example at about 30° to about 50° C. followed by a brief rinse in deionized water;

2) seed the substrate surface by placing the substrate into a mild acid solution, for example from about 1% to about 10% ascorbic acid at an elevated temperature from about 90° to about 98° C. Preferably the seeding solution is about 5% ascorbic acid and the temperature is about 95° C. The desired non-radioactive metal in an acid solution, for example Pd in about 0.1 to about 1N HCl, preferably 0.6N HCl, is added to the seeding solution and the temperature of the seeding solution is maintained. This seeding solution is maintained for a sufficient period of timing for seeding to take place, for example but not limited to 5 to about 30 minutes, more preferably for about 20 minutes. The substrate is then rinsed with deionized water and dried;

3) the pre-coated substrate is baked at a temperature below the recrystallization, or softening temperature of the substrate, for example but not limited to 100° to about 600° C. Preferably, the baking temperature is from about 350° to about 450° C. and the temperature is maintained for a period of time sufficient to harden the seeding layer onto the substrate, for example, but not limited to about 0.5 to about 2 hours. The precoated substrate is optionally washed in a salt solution, for example NaCl, for example from about 0.1% to about 5% NaCl solution, and ultrasonically treated for a period of time at an elevated temperature, for example 1 to about 15 minutes at 25° to about 75° C.

4) following a brief rinse in deionized water, the substrate is placed into a matrix solution, comprising for example, but not limited to EDTA, hydrazine sulfate, and $NH_4OH$, and the radioisotope of interest is added to the matrix solution. The matrix solution is heated at a temperature, and for a period of time sufficient to drive the radioactive isotope onto the substrate, for example from about 90° to about 95° C. for about 10 to about 90 minutes. Additional $NH_4OH$ may be added during the heating step to ensure an adequate concentration of $NH_4OH$, in the matrix solution. The substrate is briefly rinsed in deionized water and baking at a temperature below the recrystallization, or softening temperature of the substrate for example but not limited to 100° to about 600° C. Preferably, the baking temperature is from about 350° to about 450° C. and the temperature is maintained for a period of time sufficient to harden the coated layer onto the substrate, for example, but not limited to about 0.5 to about 3 hours.

5) optionally, the substrate may be rinsed and re-immersing in a second matrix solution prior to baking. The second matrix solution may comprise the same, or a new radioactive isotope, and the electroless plating step be repeated if desired.

Method B may also be carried out without a seeding step as follows:

1) preparing the surface of the substrate, for example a medical device, prior to initiating the coating procedure. This treatment may include degreasing and/or deoxidizing the surface of the substrate as described above. The substrate is then rinsed with deionized water and dried;

2) the cleaned substrate is placed into a matrix solution, comprising for example, but not limited to EDTA, hydrazine sulfate, and $NH_4OH$, and the radioisotope of interest is added to the matrix solution. The matrix solution is heated at a temperature, and for a period of time sufficient to drive the radioactive isotope onto the substrate, for example from about 90° to about 95° C. for about 10 to about 120 minutes. Additional $NH_4OH$ may be added during the heating step to ensure an adequate concentration of $NH_4OH$ in the matrix solution. The substrate is briefly rinsed in deionized water and baking at a temperature below the recrystallization, or softening temperature of the substrate for example but not limited to 100° to about 600° C. Preferably, the baking temperature is from about 350° to about 450° C. and the temperature is maintained for a period of time sufficient to harden the coated layer onto the substrate, for example, but not limited to about 0.5 to about 3 hours.

3) the substrate may be rinsed and re-immersing in a second matrix solution prior to baking. The second matrix solution may comprise the same, or a new radioactive isotope, and the electroless plating step repeated;

4) the cleaned substrate is placed into a new matrix solution, comprising similar components as for the initial electroless plating procedure, including for example, but not limited to EDTA, hydrazine sulfate, and $NH_4OH$, and a non-radioactive, overcoating metal of interest. The matrix solution is heated at a temperature, and for a period of time sufficient to drive the non-radioactive metal onto the substrate, for example from about 90° to about 95° C. for about 10 to about 120 minutes. Additional $NH_4OH$ may be added during the heating step to ensure an adequate concentration of $NH_4OH$, in the matrix solution. The substrate is briefly rinsed in deionized water and baking at a temperature below the recrystallization, or softening temperature of the substrate for example but not limited to 100° to about 600° C. Preferably, the baking temperature is from about 350° to about 450° C. and the temperature is maintained for a period of time sufficient to harden the coated layer onto the substrate, for example, but not limited to about 0.5 to about 3 hours.

5) the substrate may be rinsed and re-immersed in a second new matrix solution prior to baking, or the substrate may be overcoated after baking. The second matrix solution may comprise the same, or a new radioactive isotope, and the electroless plating step repeated;

It is contemplated that the steps of the methods of this invention can be performed either manually or automated, and cover a range of radioactivity.

Following the baking step, the uniformity of the coating on the substate may be examined. For example, which is not to be considered limiting, if the substrate is a stent, the radial uniformity (e.g. FIG. 8), as well as the axial (longitudinal) uniformity is determined (e.g. FIGS. 9 and 10). Variations in the radial and axial uniformity are less than 20%, preferably less than 15% and more preferably less than 10% (see Tables 4 to 8, Example 3).

Substrates coated by method B are tested for the adherence of the coating on the surface of the substrate. For such leach tests the substrate is placed with a saline solution, for example a 1–5% sterile solution and exposed to ultrasonic treatment for 15 minutes at 37° C. The substrate is removed and the activity of the leachate determined.

Using the above method, coated substrates, for example stents, have been produced comprising from about 1 to about 10 mCi of Pd-103. The leachate of these stents is below 1%, and typically stents are routinely produced with leachates of less than 0.5% and preferably 0.2% (see Example 3, Tables 4 to 8).

Furthermore, substrates that flex during use may be coated and the conformation of the substrate altered, such as expanding a stent, within minimal or negligible increase in the leachate. For example which is not to be considered limiting, expandable stents have been prepared and the retention of coated activity and leachate determined prior to and after stent expansion. In such studies, the retention of activity following expansion is from about 99.7% to about 99.907% of the total activity. Similarly, the leachate following expansion of the stent are still well below 2% leachate, and typically below 1%, and preferably below 0.5%, and range from about 0.093% to about 0.4% (see Table 9 in Example 3).

Electroplating Method for Coating a Substrate (Method C)

The coating of substrate using electroplating of a desired radioisotope is also considered within the scope of the present invention. Any metallic substrate, for example but not limited to, silver, palladium or rhodium may be coated with radioactive isotope of interest by electroplating. Such a coated substrate exhibits leaching rates suitable for use within biological applications. However, if desired, the coated substrate may also be radioisotope-coated with a protective layer such as a polymer, a ceramic/polymer and ceramic coating and then loaded into nylon tubing or other type of elastic tubing for use as a sealed source (as per ANSI standards). The amount of activity loaded onto the substrate can be varied through the process reaction time and the specific activity of the isotope.

The electroplating method of affixing radioisotopes onto a non-radioactive substrate is designed to achieve a uniform coverage of the substrate resulting in a predictable radiation field at a given distance from the device. The technique is applicable to any metallic substrate, for example, but not limited to silver, bronze, stainless steel, nitinol (nickel titanium alloy), zirconium, aluminum, brass, zinc, titanium, platinum, tantalum, rohdium and palladium. This method may also be used with a range of radioisotopes including, but not limited to: S-35, Cl-36, Mo-99, I-123, I-124, I-125, I-129, I-131, Pd-103, Ho-166, Y-90, P-32 and Ce-144.

The electroplating procedure utilizes an aqueous solution of a salt compatible with the isotope to be plated onto the substrate. General procedures relating to electoplating are well known within the art (e.g. ASM Handbook, Surface Engineering, Vol 5, 1990, ASM International; which is incorporated herein by reference). For example, but not to be considered limiting, NaI, or KI may be used with I-125 or related isotopes, or PdCl with Pd-103. The metallic substrate to be coated may be used as the anode or cathode as required, depending upon the charge of the isotope to be plated. For example, but not to be considered limiting, for the plating of I-125, a silver wire may be used as an anode along with a platinum wire is used as the cathode. In this combination of electrodes, platinum acts as an inert conductor, in that it does not participate in the redox chemistry, except as a conductor of electrons for other chemical reaction to occur. Other metals may be used as anode or cathodes as would be evident to one of skill in the art, for example, but not limited to palladium, rhodium, ruthenium, osmium, platinum, iridium (e.g, Raub Ch.J 1990, ASM Handbook, pp. 251–254), or silver (Blair A, 1990 ASM Handbook, pp. 245–246). In the case of electroplating I-125 onto silver wire, the pH of the solution is alkaline, preferably at about pH 10 to about pH 12.

A current is applied between the electrodes to create a potential difference between the electrodes. For example which is not to be considered limiting, in the case of I-125, a current is applied to the anode (silver wire) for a period of time sufficient to produce a uniform coating of desired activity, for example but not to be considered limiting, a current of from about 5 $\mu$A to about 50 $\mu$A, preferably from about 15 $\mu$A to about 20 $\mu$A, may be applied for about 10 min to about 5 hours. Preferably, the current is applied for about 1 to about 2 hours, however, this time may be varied as required. Following the electroplating step, the substrate is rinsed, allowed to air dry and, if required, the substrate is then baked below the recrystallization temperature of the substrate. The substrate is tested for leaching of the coated radioisotope as described above.

Approximately 3 to 5 Ci of iodine-125 (0.173 mg iodine 125 of specific activity of 17.27 Ci/mg) has been coated on the silver wire of 0.25 mm diameter and 3 cm length using the above defined method. Higher radioactivity can also be achieved.

Therefore, the present invention also provides for a method for coating a metallic medical device with a radioactive isotope comprising:

a) immersing the metallic medical device into an aqueous salt solution at an alkaline pH, and comprising a radioactive isotope, the metallic medical device acts as a first electrode;

b) inserting a second electrode with the aqueous salt solution;

c) applying a current to create a potential difference between the first and second electrodes;

d) removing the current, and rinsing the metallic medical device, allowing to air dry, and e) optionally, baking, at a temperature below the recrystallization temperature of the substrate.

The above description is not intended to limit the claimed invention in any manner, furthermore, the discussed combination of features might not be absolutely necessary for the inventive solution.

The following examples, while exemplifying the method and preparation of coated medical devices, are not to be considered limiting as to the scope of substrate, shape, or utility of devices that could be coated. Examples 1 and 2 refer to substrates coated using method A, while example 3 relates to substrates coated using method B.

EXAMPLE 1
Coating of Substrates Using Different Immersion Solutions

Different substrates were exposed to different immersion solutions containing Y-90. The solutions were heated from 50° C., and ultrasonically treated for 1–3 hours. The amount of isotope remaining on the surface of the stents was calculated from the total amount applied to the immersion matrix. The results are presented in Table 1:

TABLE 1

Coating of different substrates with Y-90 using different immersion solutions

| Substrate & Matrix | Yield |
| --- | --- |
| SS*: 1N $NH_4OH$ | 50% |
| SS: 1N $NH_4OH$ + 10% EtOH | 60% |
| SS: 5% $NH_4NO_3$ (w/v) | 0% |
| SS: $H_2O$, pH 6.0 | 40% |
| SS: 0.9–3% NaCl (w/v) | 60% |
| SS: 1% NaCl (w/v) ($NH_4OH$ to adjust pH) pH 8–9 | 50% |
| Tantalum: 1% NaCl (w/v) | 81% |
| Zirconium: 1% NaCl (w/v) | 82% |
| Plantinum: 1% NaCl (w/v) | 68% |
| TEFLON ® (PTFE) 1% NaCl + 0.1% $NaHCO_3$ (w/v) | 30% |
| Glass: 1% NaCl + 0.1% $NaHCO_3$ (w/v) | 45% |

*SS: stainless steel

The data of Table 1 indicates that Y-90 is capable of being applied to a variety of substrates, including stainless steel, tantalum, zirconium, platinum, TEFLON® and glass in the presence of saline. However, modification of the immersion matrix may have dramatic effects on the interaction between the isotope and substrate (e.g. compare $NH_4OH$ v. $NH_4NO_3$).

Furthermore, it has been observed that equivalent yields are obtained using a variety of surface geometries including, pin and button shaped substrates, or spherical or flat surfaced substrates.

EXAMPLE 2
Optimizing Coating of Substrate with Radioisotopes Using Ultrasonic Treatment Cleaning of Stent Stainless steel stents were prepared by using a citic acid and sodium citrate or $HNO_3$ cleaning solutions.

Immersion Matrix

The cleaned stents were placed into an immersion matrix within a vial so as to totally immerse the stents, followed by addition of radioisotope. The immersion matrix was either ammonia (from about 0.001 to 1N $NH_4OH$), NaCl with sodium bicarbonate, sodium carbonate, or saline (pH 8), for Y-90, sodium nitrate, or ammonium nitrate (pH 6–8) with P-32, respectively, and ethanol (10%) or saline (1%), with the radioisotope being in acid form (either HCl for Y-90 or $H_3PO_4$ for P-32).

Ultrasonic Treatment

The loaded vials were placed within an ultrasonic tank at from about 40–80° C., and exposed to tuned vibrational cavitation from 5 min, up to 3 hours. As a comparison, stents were also exposed to heat-induced evaporation in place of ultrasonic treatment. For this treatment, stents were placed on top of a hot plate (approximately 200° C.) for a period of time until dry.

Baking

The immersion matrix was decanted, and optionally the stents rinsed, dried, placed into a new vial and baked. Baking temperatures ranged from 300 to 420° C., and baking times ranged from about 30 min to 1 hour. The vial containing the stent was removed and allowed to cool.

Washing

Saline (1%) was added to the vial, and the vial placed in an ultrasonic tank for 15 min, at 50° C. Typically the protocol involves one wash step followed by 3 leaching steps as outlined below.

Leaching

Saline was added to the vial and the vial placed within an ultrasonic tank. Ultrasonic treatments lasted for 15 min at 37° C. This treatment was typically repeated three times. Aliquots of leaching solution were assayed for radioisotope contamination using a liquid scintillation measurement device (see FIGS. 5, and 6A, B).

Uniformity

Figure 7:
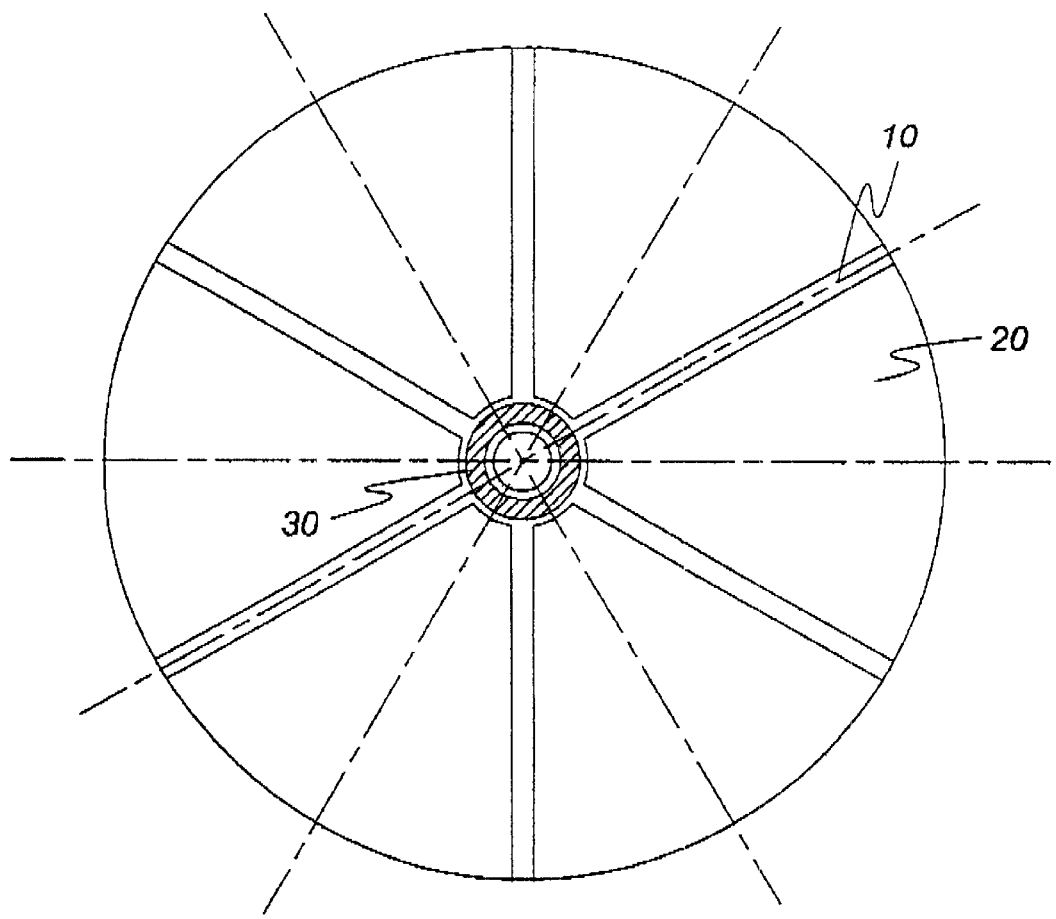
FIG. 7 represents in diagrammatic form the instrument used to test stents for their radial uniformity.
Figure 8:
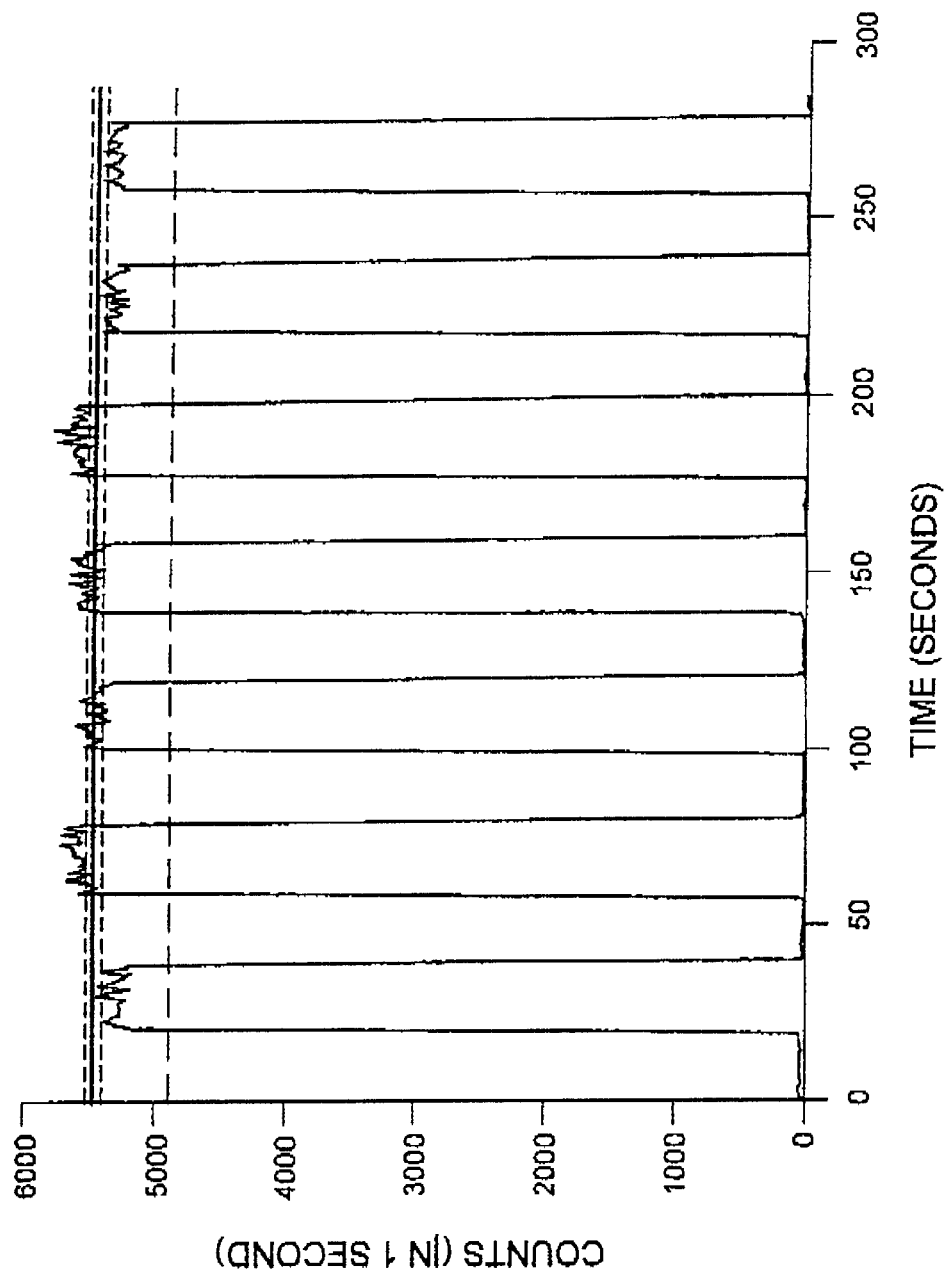
FIG. 8 shows data of uniformity scan analysing the radial uniformity of radioactive emission of a coated stent. The 7 peaks on this graph represent the detection of radioactive emission from the stent as detected using the instrument of FIG. 6.
Figure 9:
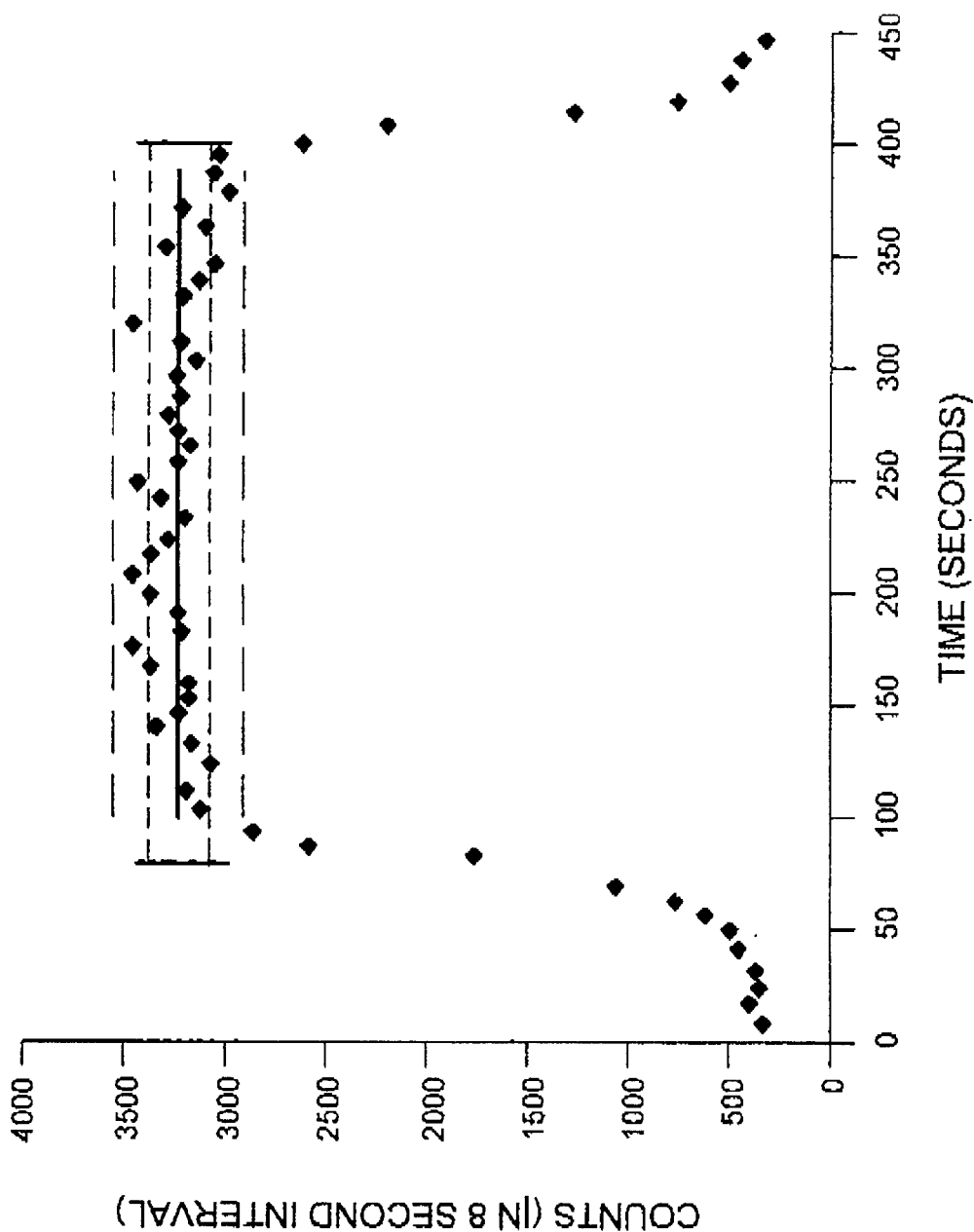
FIG. 9 shows data of a uniformity scan analysing the longitudinal uniformity of radioactive emission of a coated stent. The profile represents the detection of radioactive emission from a stent as the detector is passed along the length of the stent. The two vertical solid bars indicate the length of the stent, the horizontal solid line represents the average detected emission, the horizontal dashed and dotted lines represent deviation (total, or 3 standard deviations, respectively) from the average detected emission.

Uniformity of the radio coating of the substrate can be detected using any suitable detector. For the purposes of the following examples, a Bioscan Flow-Count radiochromatography detection system which was modified so that accurate radial and longitudinal scans of radioactively coated stents can be obtained, was used. The detector essentially comprises a variety of scintillation crystals. For radial uniformity, the detector is mounted on the outside of a shielding device (20) containing radially spaced apart slits (10; see FIG. 7) and the stent is placed centrally (30) within this device. As the shielded device revolves, any radioactive emissions that escape from the shielded device, through the slits, are registered by the fixed position detector (FIG. 8). Similarly, longitudinal uniformity is analysed by placing the coated stent within a shielded device that contains a longitudinal slit so that the radioactive emissions along the length of the stent can be determined (FIG. 9). Stents coated by the method of this invention, including tuned vibrational cavitation, wherein the yield of radioisotope is about 40–60%, the coating is uniform, both longitudinally and radially (FIGS. 8, 9 and 10A). With higher concentration of radioisotope added to the immersion matrix, and/or with shorter exposure to tuned vibrational cavitation, deviation from uniformity is observed (See FIGS. 10B and C). Even though these variations in coating uniformity are observed, different applications of stents bearing such modified coatings may be useful if higher emissions are desired at both or one end of the stent.

A) Y-90

Effect of Ultrasonic, Heating to Dryness or Reflux Treatment

Stainless steel stents were exposed for 1 hour in 1N $NH_4OH$/10% EtOH containing carrier-free Y-90 to ultrasonic or reflux treatments, or neither, but heated to dryness following a one hour exposure to the same immersion matrix. After this exposure all stents were baked at 380° C. Stents exposed to ultrasonic treatment displayed a 40% yield, while the yield of the refluxed stent was 30%, and the stent treated with the step of evaporation was variable form 10–30%. The stents that were ultasonically treated exhibited much more uniformity in their radioisotope coating compared with stents that were loaded by heating to evaporation. Furthermore, it is noted that the rate of leaching of ultrasonically treated stents is 10 fold lower than those that were refluxed or heated to evaporation.

Effect of Baking

Precleaned stainless steel stents were immersed in aqueous form carrier-free Y-90 ($NH_4OH$) in a low volume on a heated surface (immersion matrix 50–60° C.) for 25 min. The resultant labelled stents were then rinsed with water, dried in a glass vial, and baked in an oven at 350° C. for 1 hour. After a number of repeated washings (heated saline and ultrasonic, as defined above), the stents were dried. The results are exhibited in FIG. 5.

Effect of Ultrasonic Treatment

Precleaned stainless steel stents were immersed in aqueous form Y-90 (ammonium) in a low volume on a heated surface (immersion matrix 50–60° C.) for 25 min, in the presence or absence of ultrasonic treatment. The stent that was not exposed to ultrasonic treatment was dried over a hot plate (200° C.). The resultant labelled stents were then rinsed with water, dried in a glass vial, and baked in an oven at 350° C. for 1 hour. After a number of repeated washings (saline/heat/ultrasonic, as defined above), the stents were dried. The results are exhibited in FIG. 6A.

Stents exposed to the step of ultrasonic treatment continued up to 170 $\mu$Ci of affixed isotope with ±10% radial and longitudinal uniformity.

B) P-32

Effect of Cleaning Solution

Stainless steel stents were cleaned using either nitric or citric acids, and exposed to ultrasonic treatment for 1 hour at 50° C. within an ammonium nitrate immersion matrix containing carrier-free P-32. Stents cleaned with citric acid resulted in a 15% yield, while those cleaned with nitric acid demonstrated a 40% yield.

Another set of experiments were conducted with stainless steel stents cleaned with citric acid and either ultrasonically treated or refluxed for 1 hour within ammonium nitrate immersion matrix in the presence of carrier-free P-32, then baked at 380° C. for 1 hour. In either case the yield was 5%.

This indicates that the cleaning solution may have an effect on the interaction between the radioisotope and substrate. For further analysis, stents were cleaned with nitric acid.

Effect of Ultrasonic, Heating to Evaporation, or Reflux Treatments on Yield

Stents were cleaned using nitric acid, and exposed to an ammonium nitrate immersion matrix (0.05 g ammonium nitrate to 0.5 g $H_2O$) and carrier-free P-32 in the presence or absence of ultrasonic exposure at 70° C. for 1 hour. Stents that were not exposed to ultrasonic treatment were either refluxed for 1 hour, or immersed at 70° C. for 1 hour prior to being dried over a hot plate (200° C.). All stents were baked at 350° C.

Stents that were refluxed or heated to evaporation resulted in a 10% yield, while those exposed to ultrasonic treatment resulted in a 20% yield. Furthermore, the uniformity of stents that were ultrasonically treated was much greater than those that were heated. Therefore, with all other parameters being held constant, ultrasonic treatment significantly increases the yield and uniformity of the coated substrate.

Effect of Ultrasonic Treatment vs. Heating to Evaporation on Isotope Leaching

Figure 6B:
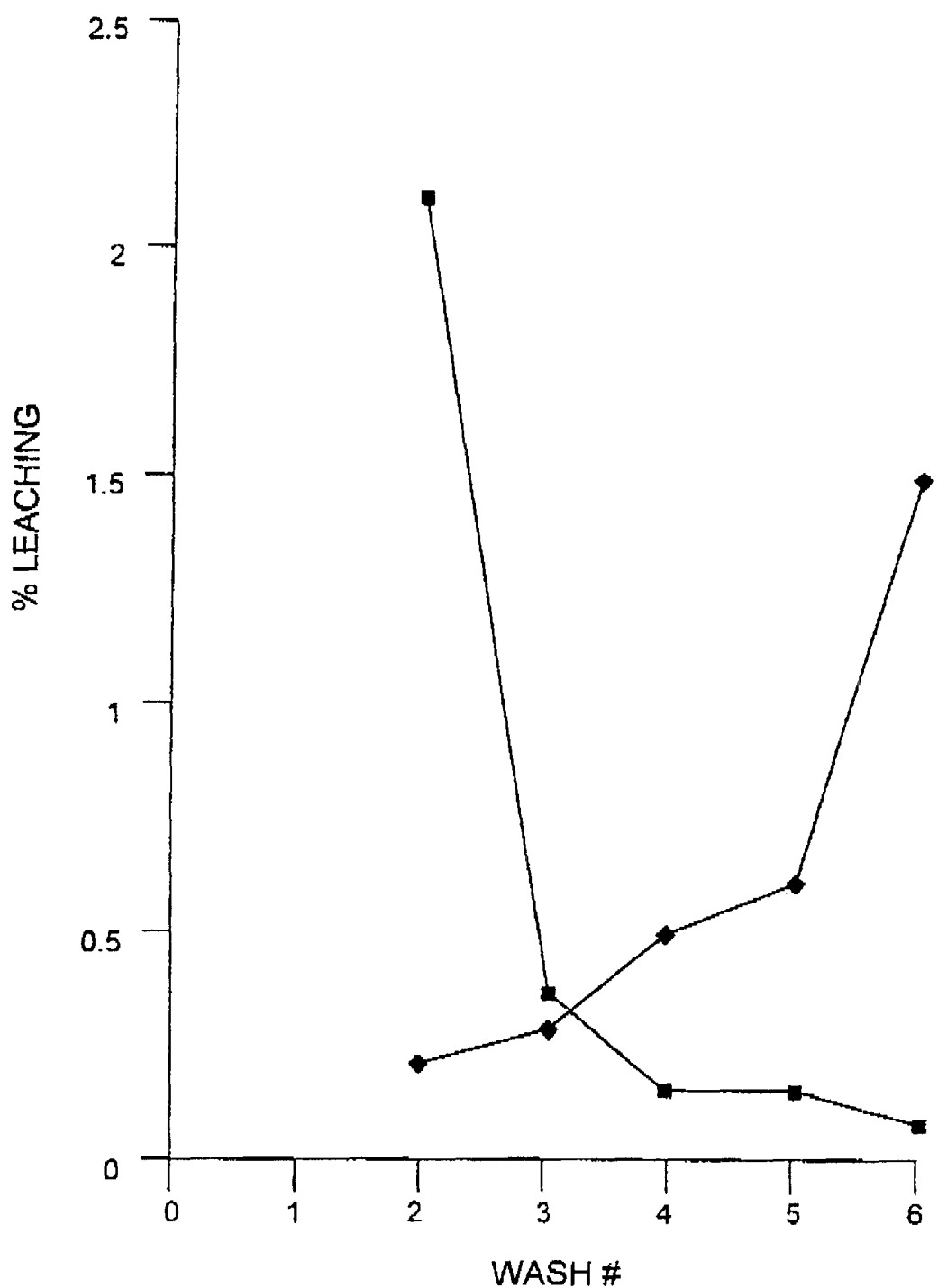

Precleaned stents were immersed in aqueous form P-32 (carrier-free) in a low volume (0.5–1.5 ml) immersion matrix containing ammonium nitrate, and either exposed to ultrasonic vibration at 60–65° C. for 25 min, or left in the immersion matrix at the same temperature for the same length of time. The stents that were not exposed to ultrasonic treatment were placed onto a heated surface (about 200° C.) and evaporated to dryness. The resultant P-32 labelled stents were then rinsed with water (2 ml), and baked in an oven (at 350–380° C. for 1 hour). After a number of repeated washings, the stent was dried. The leaching rate for these stents is presented in FIG. 6B).

Another set of experiments were performed examining the length of ultrasonic treatment on yield, wherein stents were treated to either 1 or 2 hours of ultrasonic treatment in ammonium nitrate, and baked for 1 hour at 380° C. Stents exposed to 1 hour of treatment exhibited a 30% yield, while after 2 hours they displayed a 50% yield. In both cases the uniformity was ±8%. Therefore, exposure to ultrasonic treatment results in uniform radioisotope coatings, and longer treatments results in higher yields.

Effect of Baking

Stainless steel stents were exposed to ultrasonic treatment in an ammonium nitrate immersion matrix for 25 min at 50–60° C. and treated as per the method of this invention except that some stents were not baked at 350° C. for 1 hour. Stents that were baked released 2.1, and 0.34% of the radioisotope in the first and second washes, while stents that were not baked released 9.5 and 0.76%, respectively.

In Table 2 are provided results of several runs coating stainless steel stents with P-32 using the above method involving both ultrasonic treatment and baking. The coating of nitinol stents with P-32 is presented in Table 3.

TABLE 2

P-32 Coated Stainless Steel Stents

| Radioactivity | Stent | $1^{st}$ | $2^{nd}$ | $3^{rd}$ | Total |
|---|---|---|---|---|---|
| 278 $\mu$Ci | #1 | 0.12% | 0.09% | 0.08% | 0.29% |
| 285 $\mu$Ci | #2 | 0.11% | 0.17% | 0.06% | 0.34% |
| 270 $\mu$Ci | #1 | 0.05% | 0.04% | 0.03% | 0.12% |
| 246 $\mu$Ci | #2 | 0.08% | 0.06% | 0.04% | 0.18% |
| 264 $\mu$Ci | #3 | 0.09% | 0.07% | 0.03% | 0.19% |
| 263 $\mu$Ci | #4 | 0.07% | 0.03% | 0.04% | 0.14% |
| 266 $\mu$Ci | #5 | 0.06% | 0.03% | 0.04% | 0.13% |
| 257 $\mu$Ci | #6 | 0.05% | 0.03% | 0.02% | 0.10% |

TABLE 3

P-32 Coated Nitinol Stents

| Set | % Yield | % 1 L | % 2 L | % 3 L | % Total Leach |
|---|---|---|---|---|---|
| A | 2.25 | 0.097 | 0.090 | 0.069 | 0.26 |
| A | 2.47 | 0.11 | 0.11 | 0.083 | 0.30 |

TABLE 3-continued

P-32 Coated Nitinol Stents

| Set | % Yield | % 1 L | % 2 L | % 3 L | % Total Leach |
|---|---|---|---|---|---|
| A | 2.58 | 0.16 | 0.11 | 0.049 | 0.32 |
| A | 1.82 | 0.16 | 0.14 | 0 | 0.29 |
| A | 1.93 | 0.20 | 0.17 | 0.17 | 0.54 |
| A | 2.8 | 0.071 | 0.11 | 0.21 | 0.39 |
| B | 3.15 | 0.090 | 0.077 | 0.068 | 0.24 |
| B | 3.15 | 0.19 | 0.078 | 0.073 | 0.34 |
| B | 2.62 | 0.078 | 0.18 | 0.045 | 0.30 |
| B | 2.91 | 0.13 | 0.21 | 0.12 | 0.46 |
| B | 3.02 | 0.28 | 0.086 | 0.072 | 0.44 |
| B | 2.67 | 0.17 | 0.14 | 0.072 | 0.39 |
| C | 2.98 | 0.078 | 0.046 | 0.10 | 0.23 |
| C | 2.73 | 0.059 | 0.048 | 0.14 | 0.24 |
| C | 2.85 | 0.098 | 0.094 | 0.085 | 0.28 |
| C | 3.11 | 0.053 | 0.057 | 0.14 | 0.25 |
| C | 2.62 | 0.052 | 0.074 | 0.071 | 0.20 |
| C | 2.85 | 0.056 | 0.11 | 0.13 | 0.29 |
| D | 2.49 | 0.094 | 0.066 | 0.073 | 0.23 |
| D | 2.36 | 0.10 | 0.080 | 0.16 | 0.33 |
| D | 2.87 | 0.16 | 0.14 | 0.15 | 0.44 |
| D | 1.98 | 0.15 | 0.22 | 0.25 | 0.62 |
| D | 2.49 | 0.10 | 0.069 | 0.12 | 0.29 |
| D | 2.62 | 0.11 | 0.085 | 0.095 | 0.29 |
| 1 | 10.4 | 0.043 | 0.065 | 0.026 | 0.13 |
| 2 | 7.05 | 0.11 | 0.096 | 0.2 | 0.41 |
| 3 | 6.61 | 0.16 | 0.13 | 0.074 | 0.37 |

C) Ag-110

Stainless steel stents were cleaned and exposed to ultrasonic treatment for 10 min at 50° C. within 0.1% $NaHCO_3$ containing Ag-110 (prepared via neutron bombardment of a silver target, i.e. not carrier free). Stents coated in this manner exhibited a 10% yield.

EXAMPLE 3

Coating Substrate with a Radioisotope Using Electroless Plating (with Seeding)

Cleaning

The stents were immersed in acetone for 3 to 5 minutes with agitation, rinsed and placed in a 1.0% ascorbic acid solution and sonicated for 5 minutes at 50° C. (in ultrasound bath). The stents were then rinsed in deionised $H_2O$.

Treating

The stents were immersed in 2 ml of a 5% ascorbic acid solution at 90 to 95° C. for 15 minutes.

Seeding

Non-radioactive Pd, 10 μl of a 2 mg/ml Pd in 0.6 N HCl solution was added to the heated ascorbic acid seeding solution and the solution maintained at 90–95° C. for 20 minutes. An orbital shaker was used to agitate the stents in the seeding solution. The stents were then rinsed with deionised $H_2O$, air dried and baked for 1.5 hours at between at 410° C. The stents were then washed in a 0.9% NaCl solution and subjected to ultrasonic treatment for 5 minutes at 50° C. Stents were then rinse with deionised $H_2O$ and air dried.

Coating

The stents were placed in a matrix solution comprising 0.075 g/ml EDTA, 3.75 mg/ml hydrazine sulfate, 0.75 g/ml of high purity $NH_4OH$. To this matrix solution, the amine form ($NH_4OH$) of Pd-103 is added to the desired activity. The matrix solution is heated to 90–95° C. for 50 minutes. During this step, aliquots of $NH_4OH$ are added to ensure that the volume of the matrix solution remains constant while heated. The stents are rinsed in deionized water and air dried. The yield is calculated from the activity within the matrix solution and that coated onto the sent.

Baking

The stents were baked for 2 hours at 410° C.

Leach Tests

Stents were placed in a vial comprising saline, and exposed to ultrasonic treatment for 15 min at 37° C. Aliquots of leachate were assayed for radioisotope concentration using a liquid scintillation measurement device.

Uniformity

Uniformity is determined as outlined in example 2.

Effect of Acetone Cleaning

Stainless steel stents were prepared for coating using Pd-103, as described above, however, the effect of acetone was examined at the cleaning step on leachate production of coated stents. For this analysis stents were either cleaned in the presence or absence of acetone, and then placed in a 1.0% ascorbic acid solution and sonicated for 5 minutes at 50° C. (in ultrasound bath), rinsed in deionised $H_2O$, and further processed as outlined above. The results of such an experiment are presented in Table 4.

TABLE 4

Effect of acetone cleaning on leachate - Each column represents individual production runs for Pd-103 coated stainless steel stents

| Stent # | Without acetone | | % Pd-103 leached | With Acetone | |
|---|---|---|---|---|---|
| 1 | 0.28 | 0.89 | 2.12 | 0.08 | 0.01 |
| 2 | 2.48 | 1.15 | 0.1 | 0 | 0.01 |
| 3 | 0.23 | 0.29 | 1.97 | 0.01 | 0.4 |
| 4 | 1.11 | 0.66 | 1.45 | 0.09 | 0.05 |
| 5 | 0.48 | 0.21 | 1.46 | 0.04 | 0.03 |
| 6 | 1.25 | 2.08 | 4.14 | 0 | 0.05 |
| 7 | 0.32 | 1.57 | 2.07 | 0.01 | 0 |
| 8 | 2.55 | 2.39 | 1.41 | 0.07 | 0.09 |
| 9 | 4.05 | 2.14 | 1.72 | 0.03 | 0.02 |
| 10 | 8.64 | 1.14 | 1.9 | 0.07 | |
| 11 | 10.63 | 4.57 | 1.88 | 0.06 | 0.01 |
| 12 | 11.03 | 30.89 | 0.46 | 0.24 | 0.13 |
| 13 | 2.25 | 9.44 | 1.85 | 0.01 | 0.21 |
| 14 | 3.73 | 2.99 | 0.55 | 0.45 | |
| 15 | 0.07 | 2.25 | 0.49 | | |
| 16 | 1 | 1.03 | 0.38 | | |
| 17 | 2.87 | 0.41 | | | |
| 18 | 2.21 | 7.43 | | | |
| 19 | 2.27 | 1.7 | | | |
| 20 | | 2.04 | | | |

Based on this analysis, an average leachate production of 2.8% was observed with stents that were not cleaned with acetone. With acetone cleaning, the leachate dropped to an average of 0.08. Therefore, for all further work, stainless steel stents were cleaned using acetone.

Pd-103

Following the above method, stents comprising from 1 to 10 mCi Pd-103 have been produced suitable for use within medical applications (see Tables 5–9).

TABLE 5

Properties of Stainless Steel Stents Coated with 1 mCi Pd-103

| Nominal Activity | Measured Activity | Percent Leaching | Axial Variation | Radial Variation |
|---|---|---|---|---|
| 1 mCi | 1.1 | 0.09% | 15% | 5.1% |
| 1 mCi | 1.1 | 0.03% | 10% | 1.2% |
| 1 mCi | 1.1 | 0.02% | 10% | 2.6% |
| 1 mCi | 1.1 | 0.07% | 10% | 5.8% |
| 1 mCi | 1.1 | 0.02% | 10% | 1.7% |
| 1 mCi | 1.1 | 0.10% | 10% | 4.1% |
| 1 mCi | 1.1 | 0.06% | 10% | 3.4% |

TABLE 5-continued

Properties of Stainless Steel Stents Coated with 1 mCi Pd-103

| Nominal Activity | Measured Activity | Percent Leaching | Axial Variation | Radial Variation |
|---|---|---|---|---|
| 1 mCi | 1.1 | 0.07% | 10% | 1.4% |
| 1 mCi | 1.1 | 0.07% | 10% | 2.0% |
| 1 mCi | 1.1 | 0.03% | 10% | 2.4% |
| 1 mCi | 1.1 | 0.19% | 10% | 4.5% |
| 1 mCi | 1.1 | 0.07% | 10% | 5.1% |
| 1 mCi | 1.1 | 0.09% | 10% | 6.2% |

TABLE 6

Properties of Stainless Steel Stents Coated with 1 mCi Pd-103

| Nominal Activity | Measured Activity | Percent Leaching | Axial Variation | Radial Variation |
|---|---|---|---|---|
| 2 mCi | 2.1 | 0.98 | 15% | 2.8% |
| 2 mCi | 1.9 | 0.58 | 15% | 1.7% |
| 2 mCi | 2.1 | 0.45 | 10% | 1.0% |
| 2 mCi | 2.0 | 0.52 | 10% | 1.4% |
| 2 mCi | 2.0 | 0.37 | 10% | 1.5% |
| 2 mCi | 2.0 | 0.77 | 10% | 1.6% |
| 2 mCi | 2.0 | 0.59 | 10% | 0.9% |
| 2 mCi | 2.1 | 0.47 | 10% | 1.7% |
| 2 mCi | 2.1 | 0.35 | 10% | 1.2% |
| 2 mCi | 2.0 | 0.51 | 20% | NA |
| 2 mCi | 2.1 | 0.39 | 10% | 1.3% |

TABLE 7

Properties of Stainless Steel Stents Coated with 4 mCi Pd-103

| Nominal Activity | Measured Activity | Percent Leaching | Axial Variation | Radial Variation |
|---|---|---|---|---|
| 4 mCi | 4.1 | 0.24% | 10% | 2.30% |
| 4 mCi | 3.9 | 0.38% | 10% | 1.00% |
| 4 mCi | 4.0 | 0.20% | 10% | 0.80% |
| 4 mCi | 4.2 | 0.05% | 10% | 0.40% |
| 4 mCi | 4.3 | 0.02% | 10% | 0.90% |
| 4 mCi | 4.1 | 0.09% | 10% | 0.50% |
| 4 mCi | 4.2 | 0.03% | 10% | 1.40% |
| 4 mCi | 4.0 | 0.02% | 10% | 0.90% |
| 4 mCi | 4.0 | 0.07% | 10% | 1.80% |
| 4 mCi | 4.2 | 0.27% | 10% | 1.70% |
| 4 mCi | 4.2 | 0.05% | 10% | 1.00% |
| 4 mCi | 4.0 | 0.07% | 10% | 1.30% |
| 4 mCi | 4.1 | 0.07% | 10% | 1.70% |
| 4 mCi | 4.2 | 0.01% | 10% | 1.70% |
| 4 mCi | 3.4 | 0.02% | 10% | 1.40% |

TABLE 8

Properties of Stainless Steel Stents Coated with 8 mCi Pd-103

| Nominal Activity | Measured Activity | Percent Leaching | Axial Variation | Radial Variation |
|---|---|---|---|---|
| 8 mCi | 8.0 | 0.08% | 5% | 1.37% |
| 8 mCi | 8.0 | 0.02% | 4% | 0.76% |
| 8 mCi | 8.5 | 0.00% | 7% | 1.65% |
| 8 mCi | 8.2 | 0.02% | 4% | 1.81% |
| 8 mCi | 8.3 | 0.00% | 4% | 1.59% |
| 8 mCi | 8.3 | 0.03% | 5% | 1.14% |
| 8 mCi | 8.0 | 0.06% | 8% | 1.36% |
| 8 mCi | 8.2 | 0.01% | 5% | 1.78% |
| 8 mCi | 7.8 | 0.37% | 5% | 1.67% |
| 8 mCi | 8.3 | 0.05% | 6% | 1.29% |
| 8 mCi | 7.9 | 1.03% | 5$ | 3.20% |

TABLE 8-continued

Properties of Stainless Steel Stents Coated with 8 mCi Pd-103

| Nominal Activity | Measured Activity | Percent Leaching | Axial Variation | Radial Variation |
|---|---|---|---|---|
| 8 mCi | 8.0 | 0.39% | 4% | 1.86% |
| 8 mCi | 8.1 | 0.31% | 5% | 1.06% |
| 8 mCi | 8.0 | 0.32% | 6% | 1.96% |
| 8 mCi | 8.1 | 0.35% | 6% | 2.07% |

TABLE 9

Properties of Stainless Steel Stents Coated with 10 mCi Pd-103

| Nominal Activity | Measured Activity | Percent Leaching | Axial Variation | Radial Variation |
|---|---|---|---|---|
| 10 mCi | 8.9 | 0.03% | 10% | 1.1% |
| 10 mCi | 8.7 | 0.02% | 10% | 1% |
| 10 mCi | 8.8 | 0.02% | 10% | 1.2% |
| 10 mCi | 8.8 | 0.16% | 10% | 0.7% |
| 10 mCi | 9.3 | 0.00% | 10% | 0.6% |
| 10 mCi | 9.3 | 0.02% | 10% | 1.5% |
| 10 mCi | 8.8 | 0.04% | 10% | 0.5% |
| 10 mCi | 11.0 | 0.16% | 10% | 0.7% |
| 10 mCi | 10.4 | 0.20% | 10% | 1.1% |
| 10 mCi | 10.9 | 0.08% | 10% | 0.7% |
| 10 mCi | 10.0 | 0.01% | | |
| 10 mCi | 10.2 | 0.01% | | |
| 10 mCi | 10.2 | 0.02% | | |
| 10 mCi | 10.1 | 0.01% | | |
| 10 mCi | 10.1 | 0.00% | | |
| 10 mCi | 10.0 | 0.01% | | |
| 10 mCi | 9.8 | 0.00% | | |
| 10 mCi | 10.3 | 0.01% | | |
| 10 mCi | 10.2 | 0.01% | | |
| 10 mCi | 10.5 | 0.01% | | |
| 10 mCi | 10.5 | 0.01% | | |
| 10 mCi | 10.4 | 0.01% | | |

Expanding Stents

Expandable stents are prepared as outlined above and the leachate determined following the baking step. The stent is expanded by placing it over a balloon catheter and the balloon inflated. The stent is removed and re-assayed for leaching. Result for these experiments (see Table 10) demonstrate that stents may be coated and expanded with a biological system and exhibit medically acceptable rates of leaching.

TABLE 10

Effect of expanding stent on leachate production

| Stent # | Expanded Leachings (% of Total Activity) | Original Leachings (% of Total Activity) | Expanded Retention (% of Total Activity) | Original Retention (% of Total Activity) |
|---|---|---|---|---|
| 1 | 0.297 | 0.078 | 99.703 | 99.922 |
| 2 | 0.455 | 0.017 | 99.545 | 99.983 |
| 3 | 0.227 | 0.002 | 99.773 | 99.998 |
| 4 | 0.231 | 0.022 | 99.769 | 99.978 |
| 5 | 0.187 | 0.003 | 99.813 | 99.997 |
| 6 | 0.245 | 0.028 | 99.755 | 99.972 |
| 7 | 0.314 | 0.049 | 99.686 | 99.951 |
| 8 | 0.208 | 0.021 | 99.792 | 99.979 |
| 9 | 0.040 | 0.025 | 99.960 | 99.975 |
| 10 | 0.202 | 0.033 | 99.798 | 99.967 |
| 11 | 0.098 | 0.008 | 99.902 | 99.992 |
| 12 | 0.093 | 0.004 | 99.907 | 99.996 |
| 13 | 0.153 | 0.004 | 99.847 | 99.996 |
| 14 | 0.134 | 0.008 | 99.866 | 99.992 |

TABLE 10-continued

Effect of expanding stent on leachate production

| Stent # | Expanded Leachings (% of Total Activity) | Original Leachings (% of Total Activity) | Expanded Retention (% of Total Activity) | Original Retention (% of Total Activity) |
|---|---|---|---|---|
| 16 | 0.436 | 0.013 | 99.564 | 99.987 |
| 17 | 0.428 | 0.015 | 99.572 | 99.985 |
| 18 | 0.601 | 0.001 | 99.399 | 99.999 |
| 20 | 0.799 | 0.001 | 99.201 | 99.999 |
| 1 | 0.240 | 0.063 | 99.760 | 99.937 |
| 2 | 0.092 | 0.019 | 99.908 | 99.981 |
| 3 | 0.076 | 0.374 | 99.924 | 99.626 |
| 4 | 0.186 | 0.050 | 99.814 | 99.950 |
| 5 | 0.144 | 1.033 | 99.856 | 98.967 |
| 6 | 0.103 | 1.276 | 99.897 | 98.724 |
| 7 | 0.224 | 0.388 | 99.776 | 99.612 |
| 8 | 0.065 | 0.314 | 99.935 | 99.686 |
| 9 | 0.105 | 0.319 | 99.895 | 99.681 |
| 10 | 0.252 | 0.354 | 99.748 | 99.646 |
| 11 | 0.134 | 0.821 | 99.866 | 99.179 |
| 12 | 0.212 | 0.776 | 99.788 | 99.224 |
| 13 | 0.188 | 0.427 | 99.812 | 99.573 |
| 14 | 0.059 | 0.339 | 99.941 | 99.661 |
| 15 | 0.109 | 0.570 | 99.891 | 99.430 |
| 16 | 0.075 | 0.617 | 99.925 | 99.383 |
| 17 | 0.148 | 1.280 | 99.852 | 98.720 |
| 18 | 0.340 | 0.516 | 99.660 | 99.484 |
| 19 | 0.128 | 0.349 | 99.872 | 99.651 |
| 20 | 0.201 | 0.180 | 99.800 | 99.820 |

Indium-111 coated stents

To determine if In-111 could be coated onto a substrate, stainless steel stents were prepared as follows:
stents are cleaned in 1N $HNO_3$;
In-111 (chloride, within 0.05N HCl), is used for coating;
the matrix solution comprised 0.1% $NaClO_3$ and 1% NaCl (no seeding step);
stents are immersed within matrix solution and sonicated for 10 min at 50° C.;
stents are baked at 350° C. for 1 hour, and washed at 50° C.;
leaching test involved 3 washes at 37°.

Under these non-optimized conditions leachate of 0.18, 0.09 and 0.05% were observed after the first, second and third leachings. Therefore, substrates may be coated within In-111 and produce low levels of leachate. Furthermore, with optimization of the protocol, even lower leachate production is expected. Such optimization could involve acetone cleaning, a seeding step, coating at higher temperatures, for example from about 80 to about 95° C., and backing at higher temperatures, for example form about at about 410° of, about 2 hours, as defined for the Pd-103 coating protocol.

Coating Substrate with a Radioisotope Using Electroless Plating without Seeding

Pd/Co rods that contain 93% PD and 7% Co were coated with 2–3 mG of Pd-103, and overcoated with inactive Pd on the active coating as follows:

Cleaning

The rods were immersed in acetone for 3 to 5 minutes in ultrasound bath. The rods were then rinsed in deionised $H_2O$, and cleaned in 0.1 N $HNO_3$ for 15 minutes in ultrasonic bath. Following a thorough rinse with water, the rods were baked in an oven for 10 minutes at 400° C.

Coating

To 5 ml of a matrix solution (matrix solution comprising 1.5 g EDTA, 30 mg hydrazine sulfate, and 34 ml high purity concentrated $NH_4OH$), 5 mCi of Pd-103 $[PD(NH_3)_4]Cl_2$ was added and mixed. Rods were added, and the matrix solution is heated to 90° C. for 60 minutes. During this step, 1 ml aliquots of $NH_4OH$ are added at 15, 30 and 45 min. to ensure that the volume of the matrix solution remains constant while heated. The rods were rinsed in deionized water and air dried. The yield is calculated from the activity within the matrix solution and that coated onto the sent.

Baking

The stents were baked for 1.5 to 2 hours at 400° C.

Overcoating Active Rods with Inactive Pd

Converting $PdCl_2$ to $[Pd(NH_3)_4]Cl_2$ $PdCl_2$ (0.167 g) was made up to pH 8–10 using dilute $NH_4OH$, 10 mL of water, and 5 mL of concentrated $NH_4OH$ were then added, and the mixture stirred and heated to 90° C. When the precipitate dissolved, the solution was boiled for 2 minutes, then cooled to room temperature. The pH of the solution is neutral. To this solution, $NH_4OH$ (1 mL of 10%) was added to raise pH to 8–10, and the volume brought to 100 mL using water.

Coating Rods with Inactive Pd

Five ml of a matrix solution (1.5 g EDTA, 30 mg hydrazine sulfate, and 34 ml high purity concentrated $NH_4OH$), was mixed with 100 μL of 1 mg/mL $[Pd(NH_3)_4]Cl_2$ (prepared above) and the electroless plated rod added to this mixture. The mixture was heated at 90° C. for 1 hour, and 0.5 mL conc $NH_4OH$ was added at 20, 30 and 40 minutes. The rods were rinsed well with water and baked at 400° C. for a minimum of 1.5 hours.

The overcoating step was repeated 1–3 times with leach tests after each overcoating step.

Amount of activity on rod

| Rod # | mCi of Pd-103 on rod* | Description |
|---|---|---|
| 0 | — | No cold overcoating |
| 1 | 2.2 | One cold overcoating of Pd |
| 2 | 2.2 | Two cold overcoatings of Pd |
| 3 | 3.9 | Three cold overcoatings of Pd |
| 5 | 2.3 | Five cold overcoatings of Pd |

*Calculated by difference

Dose Calibrator Readings

| Rod # | Dose Calibrator Reading (uCi) | Decay Corrected values based on reaction yield (mCi) |
|---|---|---|
| 0 | 1241 | — |
| 1 | 1510 | 1.65 |
| 2 | 1461 | 1.65 |
| 3 | 1587 | 2.9 |
| 5 | 1487 | 1.73 |

Linear Uniformity (measured using linear scanner)

| Rod # | % Linear Variation |
|---|---|
| 0 | −7% |
| 1 | 9–16% |
| 2 | 6–9% |
| 3 | 15–17% |
| 5 | 19–24% |

Leachables

Leachables were measured by immersing the rods in 50° C. saline solution for a period of 4 hours. The activity in the solution was measured using a Gamma Counter.

| Rod # | Amount of Activity in Solution (nCi) |
|---|---|
| 0 | 2.6 |
| 1 | 0.64 |
| 2 | 0.99 |
| 3 | 0.23 |
| 5 | 0.32 |

These results demonstrate that electroless plated substrates can be effectively produced without a seeding step. Furthermore, the step of overcoating helps ensure a low leach rate. However, even in the absence of an overcoating procedure, very low leach rates of less than 5 nCi are observed.

EXAMPLE 4

Electroplating a Radioactive Isotope Onto a Metallic Substrate

Electroplating of silver with I-125 involves the use of an aqueous solution of NaI, with the silver as an anode and platinum wire is used as the cathode. Platinum acts as an insert conductor, in that it does not participate in the redox chemistry, except as a conductor of electrons for other chemical reaction to occur. The pH of the solution is alkaline, preferably at about pH 10 to about pH 12.

In the case of coating silver with radioactive iodine, the half reactions of the process are as follows:

| | [E° (V)] |
|---|---|
| Half Reactions | |
| $Ag_{(s)} + I^-_{(sq)} \leftrightarrows AgI_{(a)} + 1\,e^-$ | [0.152] |
| $Ag_{(s)} \leftrightarrows Ag^+ + 1\,e^-$ | [−0.799] |
| $O_2 + 2\,H_2O + 4\,e^- \leftrightarrows 4\,OH^-$ | [0.401] |
| Reaction | |
| $4\,Ag_{(s)} + 2\,H_2O + 2\,NaI + O_2 \leftrightarrows 2\,AgI_{(s)} + 2\,Ag(OH) + 2\,NaOH$ | [−0.246] |
| or | |
| Half Reactions | |
| $Ag_{(s)} \leftrightarrows Ag^+ + 1\,e^-$ | [−0.799] |
| $O_2 + 2\,H_2O + 4\,e^- \leftrightarrows 4\,OH^-$ | [0.401] |
| Reaction | |
| $4\,Ag_{(s)} + 2\,H_2O + 2\,NaI + O_2 \leftrightarrows 2\,AgI_{(s)} + 4\,NaOH$ | [−0.398] |

This is not a spontaneous reaction as the potential (E) is negative and therefore the free energy is positive. A voltage must be applied to force the reaction to occur. The other driving force for the completion of the reaction is the high affinity of iodine for silver ($K_{sp}=1.50\times10^{-16}$ at 25° C.)

A current of 15 $\mu$A to 20 $\mu$A is applied to complete the electroplating of the silver wire with iodine -125. The reaction is carried out for about 2 hours to coat the wire with 3 Ci to 5 Ci of iodine. Once the electroplating completed the wire is rinsed with deionized water and is allowed to air dry.

Approximately 3 to 5 Ci of iodine 125 (0.173 mg iodine 125 of specific activity of 17.27 Ci/mg) has been coated on the silver wire of 0.25 mm diameter and 3 cm length. Higher radioactivity can also be achieved by varying the length of time of electroplating and the amount of isotope present within the electroplating solution.

EXAMPLE 5

The antiproliferative effect of ionizing stents, prepared using method A of this invention, on restenosis was examined within pigs. Stents were implanted using standard protocols (see Carter et al 1996) for 1 or 3 month periods. Preliminary results indicate that the rate of leaching of the coated isotope from the stent in vivo is negligible, and well within medical standards. Furthermore, results indicate that these stents prevent restenosis and inhibit vascular constriction.

The present invention has been described with regard to preferred embodiments. However, it will be obvious to persons skilled in the art that a number of variations and modifications can be made without departing from the scope of the invention as described in All scientific publications and patent documents are incorporated herein by reference.

References

Arlinghaus, H. F., Kwoka M. N., Guo, X-Q. Multiplexed DNA Sequencing and Diagnostics by Hybridization with Enriched Stable Isotope Labels. Anal. Chem. vol 69. pp. 1510–1517 (1977).

Carter, A. J., Laird J. R., Bailey, L. R., Hoopes T. G., Farb, A., Fischell, D. R., Fischell, R. E., Fischell, T. A., Virmani, R. Effects of Endovascular Radiation from a B-particle-Emitting Stent in a Porcine Coronary Restenosis Model. Circulation vol 94. pp. 2364–2368 (1996).

Corbridge. Phosphorous, and Outline of its Chemistry, Biochemistry and Uses. The Studies in Inorganic Chemistry Series. No 20. Elsevier, (1995)

Eichholz, G. G., Nagel, A. E., Hughes, R. B. Adsorption of Ions in Dilute Aqueous Solutions on Glass and Plastic Surfaces. Anal. Chem. Vol. 37, pp.863–868 (1965).

Fehsenfeld, P., Kleinraham, A., Schweikert, H. Radionuclide Technique in Mechanical Engineering in Germany. J. Radioanal. Nucl. Chem vol 160, pp. 141–151 (1991)

Fischell, T. A., Carter, A. J., Latro, J. R. The Beta-Particle-Emitting Radioisotope Stent (Isostent): Animal Studies and Planned Clinical Trials. Am J. Cardiol. vol 78 (suppl 3A), pp. 45–50 (1996).

Fischell T. A., Kharma, B. K., Fischell, D. R., Loges, P. G., Coffey II, C. W., Duggan, D. M., Naftilan A. J. Low-Dose, $\beta$-Particle Emission from 'Stent' Wire Results in Complete, Localized Inhibition of Smooth Muscle Cell Proliferation. Circulation vol 90, pp.2956–2963 (1994).

Hehrlein, C., Fehsenfeld, P. Radioactive Stents via Vascular Brachytherapy, Eds. Waksman, R., King, S. B., Crocker, I. B., Mould, R. F. Chap 21. (1996)

Hehrlein, C., Gollan, C., Donges, K., Metz, J., Riessen, R., Fehsenfeld, P., von Hodenberg, E, Kubler, W. Low Dose Radioactive Endovascular Stents Prevent Smooth Muscle Cell Proliferation and Neointimal Hyperplasia in Rabbits. Circulation vol 92, pp. 1570–1575, (1995).

Nickles, A. A., Kulago, B. R., Thomadsen, L. A., DeWerd, E. D., Werts, C. K., Stone. Making Radioactive Stents to Inhibit Restenosis Following PCTA. Proceedings of 44th Annual Meeting of Society of Nuclear Medicine, San Antonio, Tex., Jun. 1–5, (1997).

Wizemann, H. D., Niemax, K. Cancellation of Matrix Effects and Calibration by Isotope Dilution in Isotope-Selective DioideLaser Atomic Absorption Spectrometry. Annal Chem. vol 69, pp 4291–4293 (1997).

Wong, S. C., Leon, M. B. Intercoronary Stents. Curr. Opin. Cardiol. vol 10, pp. 404–411 (1995).

Violaris, A. G., Ozaki, Y., Serruys, P. W. Endovascular Stents: a 'break through technology', future challenges. Int. J. Cardiac Imaging vol 13, pp.3–13 (1997).

The embodiments of the invention in which an exclusive property or prigilege is claimed are defined as follows:

1. A method for coating a substrate with a radioisotope comprising:

a) immersing said substrate within an electroless matrix solution containing a γ, β⁺, α or β⁻ emitting radioisotope of an element selected from the group consisting of C-14, S-35, Ni, Au, Cu, Mo, Sn, Co, Ir, Rh, Re, W, Fe, B, Ru, Pd, Zn, Cd, Pb, In, Ag, Hg, Os, Tc, Ga, Sb, Bi, As, Gd, Yb, At, Cl-36, I, Ge, Si, Nb, Sc, Pm-142, Am-241, Ba, Cs, Rb, Na, K, Tl, Ir, Ta, Se, Sm, Mg, Li, Ho, Ca and Bi, at a temperature of between 90° and 95° C. to produce a coated substrate; and b) baking said coated substrate at a temperature below the recrystallization temperature of said substrate.

2. The method of claim 1 wherein in said step of immersing, step a), said matrix solution comprises a reducing agent and a stabilizing agent.

3. The method of claim 2, wherein said step of baking, step b), is followed by:

c) immersing said coated substrate with a matrix solution containing an overcoating metal at a temperature of between 90° and 95° C. to produce an overcoated substrate; and d) baking said overcoated substrate at a temperature below the recrystallization temperature of said substrate.

4. The method of claim 2, wherein said radioisotope is selected from the group of Pd-103, Pd-112, Co-55, Co-57, Co-60, Ag-110, Ag-111, Ag-112, Ag-113, Au-199, Cu-64, Re-186, Re-188, Ir-192, Ir-194, Mo-99, Ni-63, In-111, Tc-99m, C-14, S-35, Cl-36, I-125, I-131, I-123, I-124, At-211, Ge-68 Ho-166, Gd-159, Pm-142, Gd-153, Yb-169, Am-241, and Yb-160.

5. The method of claim 4, wherein said metallic radioisotope is Pd-103.

6. The method of claim 3, wherein said radioisotope is selected from the group consisting of Pd-103, Pd-112, Co-55, Co-57, Co-60, Ag-110, Ag-111, Ag-112, Ag-113, Au-199, Cu-64, Re-186, Re-188, Ir-192, Ir-194, Mo-99, Ni-63, In-111, Tc-99m, C-14, S-35, Cl-36, I-125, I-131, I-123, I-124, At-211, Ge-68, Ho-166, Gd-159, Pm-142, Gd-153, Yb-169, Am-241, and Yb-160.

7. The method of claim 6, wherein said metallic radioisotope is Pd-103.

8. The method of claim 7, wherein said overcoating metal is Pd.

9. The method of claim 2 wherein said stabilizing agent is EDTA and said reducing agent is hydrazine sulfate.

10. The method of claim 9 wherein the pH of said matrix solution is from about 7 to about 12.

11. The method of claim 1, wherein, in said step of baking, step b), said coated substrate is baked at a temperature from about 250° to about 800° C.

12. The method of claim 3, wherein, in said step of baking, step d), said overcoated substrate is baked at a temperature from about 250° to about 800° C.

13. The method of claim 11, wherein said coated substrate is baked at a temperature from about 350° to about 450° C.

14. The method of claim 12, wherein said coated substate is baked at a temperature from about 350° to about 450° C.

15. The method of claim 1 wherein step b) is followed by a step for determining leachate of said metallic radioisotope from said coated substrate.

16. The method of claim 3 wherein step d) is followed by a step for determining leachate of said metallic radioisotope from said coated substrate.

17. The method of claim 1, wherein steps a) and b) are automated.

18. The method of claim 3, wherein steps a) through to d) are automated.

19. The method of claim 1, wherein said substrate is a medical device.

20. The method of claim 19 wherein said medieal device can comprise a variety of surface geometries, and is selected from the group consisting of: stent, expandable stent, needle, catheter source for after-loader, source for brachytherapy, brachytherapy seed, delivery wire, seed, wire, protheses, valves, suture, and staples.

21. The method of claim 20 wherein the medical device is a stent.

22. The method of claim 20 wherein the medical device is a wire.

23. The method of claim 20 wherein the medical device is a seed.

24. The method of claim 1 wherein said substrate is metallic.

25. The method of claim 1 wherein the substrate is stainless steel.

26. The method of claim 1 wherein the substrate is nitinol.

27. The method of claim 1, wherein said radioisotope is selected from the group consisting of Pd-103, Pd-112, Co-55, Co-57, C-60, Cu-64, Re-186, Re-188, Ir-192, Ir-194, Mo-99, Ni-63, Yb-169, and Yb-160.

28. The method of claim 27, wherein said substrate used in step a) is pre-cleaned.

29. The method of claim 3, wherein said radioisotope is selected from the group consisting of Pd-103, Pd-112, Co-55, Co-57, C-60, Cu-64, Re-186, Re-188, Ir-192, Ir-194, Mo-99, Ni-63, Yb-169, and Yb-160.

30. The method of claim 29, wherein said substrate used in step a) is pre-cleaned.

* * * * *